United States Patent
Penner et al.

(10) Patent No.: US 7,452,675 B2
(45) Date of Patent: Nov. 18, 2008

(54) METHODS OF SCREENING FOR TRPM4B MODULATORS

(75) Inventors: Reinhold Penner, Honolulu, HI (US); Andrea Fleig, Honolulu, HI (US)

(73) Assignee: The Queen's Medical Center, Honolulu, HI (US)

( * ) Notice: Subject to any disclaimer, the term of this patent is extended or adjusted under 35 U.S.C. 154(b) by 0 days.

(21) Appl. No.: 10/142,649

(22) Filed: May 8, 2002

(65) Prior Publication Data

US 2003/0143557 A1 Jul. 31, 2003

Related U.S. Application Data

(60) Provisional application No. 60/351,938, filed on Jan. 25, 2002, provisional application No. 60/377,937, filed on May 2, 2002.

(51) Int. Cl.
*G01N 33/53* (2006.01)
*C12P 21/02* (2006.01)

(52) U.S. Cl. ................... 435/7.1; 435/6; 435/4; 435/DIG. 3; 435/DIG. 2

(58) Field of Classification Search ............... 435/7.1, 435/4, 6, DIG. 3, DIG. 2
See application file for complete search history.

(56) References Cited

U.S. PATENT DOCUMENTS

2002/0142377 A1* 10/2002 Glucksmann et al. ...... 435/69.1

FOREIGN PATENT DOCUMENTS

WO WO 98/08979 * 3/1998
WO WO 00/40614 A2 7/2000

OTHER PUBLICATIONS

Xu et al, PNAS USA 98(19), 10692-7 (Sep. 11, 2001).*
Yellen, Nature, 296, (Mar. 25, 1982), 357-59.*
Perraud et al, Nature, 411, May 31, 2001, 595-599.*
Rowe et al, British Journal of Pharmocology, 1997, 121(3), 531-39.*
Kaiho et al, Journal of Neurochemistry, 1996, 67(1), 398-406.*
Saitow et al , Biochimica et Biophysica Acta, 1327, 52-60, 1997.*
Harteneck, Naunyn-Schmiedeberg's Arch Pharmacol. 371, 307-314, 2005.*
Launay, P, et al., TRPM4 is a Ca2+-activated nonselective cation channel mediating cell membrane depolarization. Cell. May 3, 2002;109(3):397-407.
Montell, C., et al., "A unified nomenclature for the superfamily of TRP cation channels," *Mol. Cell* 9(2):229-231 (Feb. 2002).
Runnels, L., et al., "TRP-PLIK, a bifunctional protein with kinase and ion channel activities," *Science* 291(5506):1043-1047 (2001).
Sano, Y., et al., "Immunocyte Ca2+ influx system mediated by LTRPC2," *Science* 293(5533):1327-1330 (2001).
Scharenberg, A., (Direct Submission), NCBI Accession No. AAY95436, Oct. 10, 2000.

* cited by examiner

*Primary Examiner*—T. D. Wessendorf
(74) *Attorney, Agent, or Firm*—Richard F. Trecartin; Gargi Talukder; Morgan Lweis & Bockius LLP

(57) ABSTRACT

The invention relates, in part, to methods useful in identifying molecules, that bind TRPM4*b*, which modulate TRPM4*b* ion channel activity, and/or which alter expression of TRPM4*b* within cells. The TRPM4*b* channels as described herein contain TRPM4*b* polypeptides, which are in turn encoded by TRPM4*b* nucleic acids. The ion channels described herein are preferably formed in HEK-293 cells from one or more novel TRPM4*b* polypeptides, which exhibit one or more of the unique TRPM4*b* properties described herein.

5 Claims, 10 Drawing Sheets

Figure 7

```
ggtctggaag cagagccggc ggagggagcg ccggggccct gggctgcagg aggttgcggc    60
ggccgcggca gcatggtggt gccggagaag gagcagagct ggatccccaa gatcttcaag   120
aagaagacct gcacgacgtt catagttgac tccacagatc cggagggac ccttgtgccag   180
tgtgggcgcc cccggaccgc ccaccccgca gtggccatgg aggatgcctt cggggcagcc   240
gtggtgaccg tgtgggacag cgatgcacac accacggaga agcccaccga tgcctacgga   300
gagctggact tcacggggc ccgccgcaag cacagcaatt tcctccggct ctctgaccga   360
acggatccag ctgcagttta tagtctggtc acacgcacat ggggcttccg tgccccgaac   420
ctggtggtgt cagtgctggg gggatcgggg ggcccccgtcc tccagacctg gctgcaggac   480
ctgctgcgtc gtgggctggt gcgggctgcc cagagcacag gagcctggat tgtcactggg   540
ggtctgcaca cgggcatcgg ccggcatgtt ggtgtggctg tacgggacca tcagatggcc   600
agcactgggg gcaccaaggt ggtggccatg ggtgtggccc cctggggtgt ggtccggaat   660
agagacaccc tcatcaaccc caaggggctcg ttccctgcga ggtaccggtg gcgcggtgac   720
ccggaggacg gggtccagtt tccctgac tacaactact cggccttctt cctggtggac   780
gacggcacac acggctgcct ggggggcgag aaccgcttcc gcttgcgcct ggagtcctac   840
atctcacagc agaagacggg cgtgggaggg actggaattg acatccctgt cctgctcctc   900
ctgattgatg gtgatgagaa gatgttgacg cgaatagaga acgccaccca ggctcagctc   960
ccatgtctcc tcgtggctgg ctcaggggga gctgcggact gcctggccgga gacctggaa  1020
gacactctgg ccccaggag tggggagcc aggcaaggcg aagcccgaga tcgaatcagg   1080
cgtttctttc ccaaggggga ccttgaggtc ctgcaggccc aggtggagag cattatgacc  1140
cggaaggagc tcctgacagt ctattcttct gaggatgggt ctgaggaatt cgagaccata  1200
gtttttgaagg cccttgtgaa ggcctgtggg agctcggagg cctcagccta cctggatgag  1260
ctgcgtttgg ctgtggcttg gaaccgcgtg gacattgccc agagtgaact ctttcggggg  1320
gacatccaat gccggtcctt ccatctcgaa gcttccctca tggacgccct gctgaatgac  1380
cggcctgagt tcgtgcgctt gctcattccc cacggcctca gctgggcca cttcctgacc  1440
ccgatgcgcc tggcccaact ctacagcgcg gcgccctcca actcgctcat ccgcaaccttt  1500
ttggaccagg cgtcccacag cgcaggcacc aaagcccccag ccctaaaagg gggagctgcg  1560
gagctccggc ccctgacgt ggggcatgtg ctgaggatgc tgctggggaa gatgtgcgcg  1620
ccgaggtacc cctccggggg cgcctgggac cctcacccga gccagggctt cgggagagc   1680
atgtatctgc tctcggacaa ggccacctcg ccgctctcgc tggatgctgg cctcgggcag  1740
gccccctgga gcgacctgct tctttgggca ctgttgctga cagggcaca gatggccatg  1800
tacttctggg agatgggtc caatgcagtt tcctcagctc ttggggcctg tttgctgctc  1860
cgggtgatgg cacgcctgga gcctgacgct gaggaggcag cacggaggaa agacctggcg  1920
ttcaagtttg aggcgatggg cgttgacctc tttggcgagt gctatcgcag cagtgaggtg  1980
agggctgccc ggctcctcct ccgtcgctgc ccgtctctgg gggatgccac ttgcctccag  2040
ctggccatgc aagctgacgc ccgtgccttc tttgcccagg atgggtaca gtctctgctg  2100
acacagaagt ggtggggaga tatggccagc actacaccca tctgggccct ggttctcgcc  2160
ttctttttgcc ctccactcat ctacacccgc ctcatcacct tcaggaaatc agaagaggag  2220
cccacacggg aggagctaga gtttgacatg gatagtgtca ttaatgggga agggcctgtc  2280
gggacggcgg acccagccga gaagacgccg ctggggtcc cgcgccagtc gggccgtccg  2340
ggttgctgcg ggggccgctg cggggccgct ccgtgcctgg ccgcgtggtt ccacttctgg  2400
ggcgcgccgg tgaccatctt catggccaac gtggtcagct acctgctgtt cctgctgctt  2460
ttctcgcggg tgctgctcgt ggatttccag ccggcgccgc ccggctccct ggagctgctg  2520
ctctatttct gggctttcac gctgctgtgc gaggaactgc gccagggcct gagcggaggc  2580
gggggcagcc tcgccagcgg gggcccccggg cctggccatg cctcactgag ccagcgcctg  2640
cgcctctacc tcgccgacag ctggaaccag tgcgacctag tggctctcac ctgcttcctc  2700
ctgggcgtgg gctgccggct gaccccgggt ttgtaccacc tgggccgcac tgtcctctgc  2760
atcgacttca tggttttcac ggtgcggctg cttcacatct tcacggtcaa caaacagctg  2820
gggcccaaga tcgtcatcgt gagcaagatg atgaaggacg tgttcttctt cctcttcttc  2880
ctcggcgtgt ggctggtagc ctatggcgtg gccacggagg ggctcctgag gccacgggac  2940
agtgacttcc caagtatcct gcgccgcgtc ttctaccgtc cctacctgca gatcttcggg  3000
cagattcccc aggaggacat ggacgtggcc ctcatggagc acagcaactg ctcgtcggag  3060
cccggcttct gggcacaccc tcctgggcc caggcgggca ctgcgtctc ccagtatgcc  3120
aactggctgg tggtgctgct cctcgtgctc ttcctgctcg tggccaacat cctgctgctg  3180
aacttgctca ttgccatgtt cagttacaca ttcggcaaag tacaggcaa cagcgatctc  3240
tactggaagg cgcagcgtta ccgcctcatc cgggaattcc actctcggcc cgcgctggcc  3300
ccgccctta tcgtcatctc ccacttgcgc ctcctgctca ggcaattgtg caggcgaccc  3360
cggagccccc agccgtcctc ccggccctc gagcatttcc gggtttacct ttctaaggaa  3420
gccgagcgga agctgctaac gtgggaatcg gtgcataagg agaactttct gctggcacgc  3480
gctagggaca agcgggagag cgactccgag cgtctgaagc gcacgtccca gaaggtggac  3540
ttggcactga aacagctgga acacatccgc gagtacgaac agcgcctgaa agtgcggag  3600
cgggaggtcc agcagtgtag ccgcgtcctg gggtgggtgg ccgaggccct gagccgctct  3660
gccttgctgc ccccaggtgg gccgccaccc cctgacctgc ctgggtccaa agactgagcc  3720
ctgctggcgg acttcaagga gaagcccca cagggattt tgctcctaga gtaaggctca  3780
tctgggcctc ggccccgca cctggtggcc ttgtccttga ggtgagccc atgtccatct  3840
gggccactgt caggaccacc tttgggagtg tcatccttac aaaccacagc atgcccggct  3900
cctccagaa ccagtcccag cctgggagga tcaaggcctg gatccggc cgttatccat  3960
ctggaggctg caggtccttg gggtaacag ggaccacaga cccctcacca ctcacagatt  4020
cctcacactg cgggaaataa gccatttcag aggaaaaaaa a                      4061
```

Figure 8

```
Met Val Val Pro Glu Lys Glu Gln Ser Trp Ile Pro Lys Ile Phe Lys
 1           5                   10              15
Lys Lys Thr Cys Thr Thr Phe Ile Val Asp Ser Thr Asp Pro Gly Gly
            20              25              30
Thr Leu Cys Gln Cys Gly Arg Pro Arg Thr Ala His Pro Ala Val Ala
        35              40              45
Met Glu Asp Ala Phe Gly Ala Ala Val Val Thr Val Trp Asp Ser Asp
 50              55                   60
Ala His Thr Thr Glu Lys Pro Thr Asp Ala Tyr Gly Glu Leu Asp Phe
 65              70                  75                      80
Thr Gly Ala Gly Arg Lys His Ser Asn Phe Leu Arg Leu Ser Asp Arg
                85              90                      95
Thr Asp Pro Ala Ala Val Tyr Ser Leu Val Thr Arg Thr Trp Gly Phe
            100             105             110
Arg Ala Pro Asn Leu Val Val Ser Val Leu Gly Gly Ser Gly Gly Pro
            115             120             125
Val Leu Gln Thr Trp Leu Gln Asp Leu Leu Arg Arg Gly Leu Val Arg
    130             135             140
Ala Ala Gln Ser Thr Gly Ala Trp Ile Val Thr Gly Gly Leu His Thr
145             150             155                     160
Gly Ile Gly Arg His Val Gly Val Ala Val Arg Asp His Gln Met Ala
            165             170             175
Ser Thr Gly Gly Thr Lys Val Val Ala Met Gly Val Ala Pro Trp Gly
            180             185             190
Val Val Arg Asn Arg Asp Thr Leu Ile Asn Pro Lys Gly Ser Phe Pro
        195             200             205
Ala Arg Tyr Arg Trp Arg Gly Asp Pro Glu Asp Gly Val Gln Phe Pro
    210             215             220
Leu Asp Tyr Asn Tyr Ser Ala Phe Phe Leu Val Asp Asp Gly Thr His
225             230             235                     240
Gly Cys Leu Gly Gly Glu Asn Arg Phe Arg Leu Arg Leu Glu Ser Tyr
                245             250             255
Ile Ser Gln Gln Lys Thr Gly Val Gly Gly Thr Gly Ile Asp Ile Pro
            260             265             270
Val Leu Leu Leu Leu Ile Asp Gly Asp Glu Lys Met Leu Thr Arg Ile
        275             280             285
Glu Asn Ala Thr Gln Ala Gln Leu Pro Cys Leu Leu Val Ala Gly Ser
    290             295             300
Gly Gly Ala Ala Asp Cys Leu Ala Glu Thr Leu Glu Asp Thr Leu Ala
305             310             315                     320
Pro Gly Ser Gly Gly Ala Arg Gln Gly Glu Ala Arg Asp Arg Ile Arg
                325             330             335
Arg Phe Phe Pro Lys Gly Asp Leu Glu Val Leu Gln Ala Gln Val Glu
            340             345             350
Arg Ile Met Thr Arg Lys Glu Leu Leu Thr Val Tyr Ser Ser Glu Asp
        355             360             365
Gly Ser Glu Glu Phe Glu Thr Ile Val Leu Lys Ala Leu Val Lys Ala
    370             375             380
Cys Gly Ser Ser Glu Ala Ser Ala Tyr Leu Asp Glu Leu Arg Leu Ala
385             390             395                     400
Val Ala Trp Asn Arg Val Asp Ile Ala Gln Ser Glu Leu Phe Arg Gly
            405             410             415
Asp Ile Gln Trp Arg Ser Phe His Leu Glu Ala Ser Leu Met Asp Ala
        420             425             430
Leu Leu Asn Asp Arg Pro Glu Phe Val Arg Leu Leu Ile Ser His Gly
    435             440             445
Leu Ser Leu Gly His Phe Leu Thr Pro Met Arg Leu Ala Gln Leu Tyr
450             455             460
Ser Ala Ala Pro Ser Asn Ser Leu Ile Arg Asn Leu Leu Asp Gln Ala
465             470             475                     480
Ser His Ser Ala Gly Thr Lys Ala Pro Ala Leu Lys Gly Gly Ala Ala
            485             490             495
```

FIGURE 8 (cont.)

```
Glu Leu Arg Pro Pro Asp Val Gly His Val Leu Arg Met Leu Leu Gly
            500             505             510
Lys Met Cys Ala Pro Arg Tyr Pro Ser Gly Gly Ala Trp Asp Pro His
        515             520             525
Pro Gly Gln Gly Phe Gly Glu Ser Met Tyr Leu Leu Ser Asp Lys Ala
        530             535             540
Thr Ser Pro Leu Ser Leu Asp Ala Gly Leu Gly Gln Ala Pro Trp Ser
545             550             555                         560
Asp Leu Leu Leu Trp Ala Leu Leu Leu Asn Arg Ala Gln Met Ala Met
                565             570             575
Tyr Phe Trp Glu Met Gly Ser Asn Ala Val Ser Ser Ala Leu Gly Ala
            580             585             590
Cys Leu Leu Leu Arg Val Met Ala Arg Leu Glu Pro Asp Ala Glu Glu
            595             600             605
Ala Ala Arg Arg Lys Asp Leu Ala Phe Lys Phe Glu Gly Met Gly Val
        610             615             620
Asp Leu Phe Gly Glu Cys Tyr Arg Ser Ser Glu Val Arg Ala Ala Arg
625             630             635                         640
Leu Leu Leu Arg Arg Cys Pro Leu Trp Gly Asp Ala Thr Cys Leu Gln
                645             650             655
Leu Ala Met Gln Ala Asp Ala Arg Ala Phe Phe Ala Gln Asp Gly Val
            660             665             670
Gln Ser Leu Leu Thr Gln Lys Trp Trp Gly Asp Met Ala Ser Thr Thr
            675             680             685
Pro Ile Trp Ala Leu Val Leu Ala Phe Phe Cys Pro Pro Leu Ile Tyr
        690             695             700
Thr Arg Leu Ile Thr Phe Arg Lys Ser Glu Glu Glu Pro Thr Arg Glu
705             710             715                         720
 Glu Leu Glu Phe Asp Met Asp Ser Val Ile Asn Gly Glu Gly Pro Val
                725             730             735
 Gly Thr Ala Asp Pro Ala Glu Lys Thr Pro Leu Gly Val Pro Arg Gln
            740             745             750
 Ser Gly Arg Pro Gly Cys Cys Gly Gly Arg Cys Gly Gly Arg Arg Cys
            755             760             765
 Leu Arg Arg Trp Phe His Phe Trp Gly Ala Pro Val Thr Ile Phe Met
        770             775             780
 Gly Asn Val Val Ser Tyr Leu Leu Phe Leu Leu Leu Phe Ser Arg Val
 785             790             795             800
 Leu Leu Val Asp Phe Gln Pro Ala Pro Pro Gly Ser Leu Glu Leu Leu
                805             810             815
 Leu Tyr Phe Trp Ala Phe Thr Leu Leu Cys Glu Glu Leu Arg Gln Gly
            820             825             830
 Leu Ser Gly Gly Gly Gly Ser Leu Ala Ser Gly Gly Pro Gly Pro Gly
            835             840             845
 His Ala Ser Leu Ser Gln Arg Leu Arg Leu Tyr Leu Ala Asp Ser Trp
 850             855             860
 Asn Gln Cys Asp Leu Val Ala Leu Thr Cys Phe Leu Leu Gly Val Gly
 865             870             875             880
 Cys Arg Leu Thr Pro Gly Leu Tyr His Leu Gly Arg Thr Val Leu Cys
                885             890             895
 Ile Asp Phe Met Val Phe Thr Val Arg Leu Leu His Ile Phe Thr Val
            900             905             910
 Asn Lys Gln Leu Gly Pro Lys Ile Val Ile Val Ser Lys Met Met Lys
            915             920             925
 Asp Val Phe Phe Phe Leu Phe Phe Leu Gly Val Trp Leu Val Ala Tyr
        930             935             940
 Gly Val Ala Thr Glu Gly Leu Leu Arg Pro Arg Asp Ser Asp Phe Pro
 945             950             955             960
 Ser Ile Leu Arg Arg Val Phe Tyr Arg Pro Tyr Leu Gln Ile Phe Gly
                965             970             975
 Gln Ile Pro Gln Glu Asp Met Asp Val Ala Leu Met Glu His Ser Asn
            980             985             990
 Cys Ser Ser Glu Pro Gly Phe Trp Ala His Pro Pro Gly Ala Gln Ala
            995             1000            1005
```

Figure 8 (cont.)

```
Gly Thr Cys Val Ser Gln Tyr Ala Asn Trp Leu Val Val Leu Leu Leu
    1010                1015                1020
Val Ile Phe Leu Leu Val Ala Asn Ile Leu Leu Val Asn Leu Leu Ile
1025            1030                1035                1040
Ala Met Phe Ser Tyr Thr Phe Gly Lys Val Gln Gly Asn Ser Asp Leu
                1045                1050                1055
Tyr Trp Lys Ala Gln Arg Tyr Arg Leu Ile Arg Glu Phe His Ser Arg
                1060            1065            1070
Pro Ala Leu Ala Pro Pro Phe Ile Val Ile Ser His Leu Arg Leu Leu
            1075            1080            1085
Leu Arg Gln Leu Cys Arg Arg Pro Arg Ser Pro Gln Pro Ser Ser Pro
    1090            1095            1100
Ala Leu Glu His Phe Arg Val Tyr Leu Ser Lys Glu Ala Glu Arg Lys
1105            1110            1115                1120
Leu Leu Thr Trp Glu Ser Val His Lys Glu Asn Phe Leu Leu Ala Arg
                1125            1130            1135
Ala Arg Asp Lys Arg Glu Ser Asp Ser Glu Arg Leu Lys Arg Thr Ser
            1140            1145            1150
Gln Lys Val Asp Leu Ala Leu Lys Gln Leu Gly His Ile Arg Glu Tyr
    1155            1160            1165
Glu Gln Arg Leu Lys Val Leu Glu Arg Glu Val Gln Gln Cys Ser Arg
    1170            1175            1180
Val Leu Gly Trp Val Ala Glu Ala Leu Ser Arg Ser Ala Leu Leu Pro
1185            1190            1195            1200
Pro Gly Gly Pro Pro Pro Asp Leu Pro Gly Ser Lys Asp
            1205            1210
```

METHODS OF SCREENING FOR TRPM4B MODULATORS

CROSS-REFERENCE

This application claims priority to (1) U.S. provisional application Ser. No. 60/351,938, filed Jan. 25, 2002, entitled "LTRPC4 is a $CA^{2+}$-Activated Non-Selective Cation Channel Mediating Cell Membrane Depolarization" and (2) U.S. provisional application Ser. No. 60/377,937, filed May 2, 2002, entitled "Methods of Screening for TRPM4b Modulators."

FIELD OF THE INVENTION

The present invention relates to the use of a novel family of Calcium-Activated Nonselective ("CAN") transmembrane channel polypeptides designated herein as "TRPM4b".

BACKGROUND OF THE INVENTION

Ion channels are transmembrane multi-subunit proteins embedded in the cellular plasma membranes of living cells which permit the passage of specific ions from the extracelluar side of the plasma membrane to the intracellular region of the cell. Specific ion transport is facilitated by a central aqueous pore which is capable of opening and closing due to changes in pore conformation. When the ion gate is open, ions flow freely through the channel. When the ion gate is closed, ions are prevented from permeating the channel. Ion channels are found in a multitude of multicellular eukaryotic species and in a myriad of different cell types. Ion channels may be either voltage-gated or ligand-gated. Channel gating is the process by which a particular channel is either open or closed. An ion channel may be capable of occupying a range of different "open" or "closed" states. The gating process may therefore require a particular sequence of transition states or inclusion of alternative transition states before a channel attains a particular level of gating. The gating process is modulated by a substance or agent, which in some way alters or affects the manner in which the channel opens or closes. A channel may be gated by a ligand such as a neurotransmitter, an internal primary or secondary messenger, or other bioactive agent. The ligand either attaches to one or more binding sites on the channel protein or attaches to a receptor that is associated with the channel. If the channel-is voltage-gated, changes in the membrane potential trigger channel gating by conformational changes of charged elements within the channel protein. Whether a channel is ligand-gated or voltage-gated, a change in one part of the channel produces an effect in a different part of the channel which results in the opening or closing of a permeant pathway.

The non-selective transmembrane channel polypeptides form a family of cation channels comprised of seven members TRPC1-TRPC7. The channel proteins are further divided into three main subfamilies: S for Short non-selective transmembrane channels, L for long non-selective transmembrane channels, and O for Osm-9-like non-selective transmembrane channels. Although the non-selective ion channel proteins are widely distributed in mammalian tissues, the specific physiological properties of the channels remain largely unknown. The protein subunits of the non-selective transmembrane channels have six transmembrane domains predicted to assemble into tetramers for forming ionic channels. The slightly hydrophobic amino acids which link the fifth and sixth transmembrane domain are purported to line the pores of the channels. Amino terminal and carboxyl terminal domains of the non-selective protein comprise the intracytoplasmic region of the channel. In spite of similarities in structure, the functions of the non-selective channel proteins differ between members of the same polypeptide family. Studies demonstrate that each channel has a unique ion selectivity and a particular mechanism for activation.

SUMMARY OF THE INVENTION

The invention relates to the use of a novel family of Calcium-Activated Nonselective ("CAN") transmembrane channel polypeptides designated herein as "TRPM4b". TRPM4b channels are specifically activated by elevations in cytoplasmic $Ca^{2+}$ in the nanomolar range, may be directly gated by $Ca^{2+}$, conduct monovalent cations such as $Na^+$, $K^+$, and $Cs^+$ without significant $Ca^{2+}$ permeation, are activated subsequent to receptor-mediated $Ca^{2+}$-mobilization, support important cellular responses such as neuronal bursting activity, kidney cell osmotic regulation and/or cardiac rhythmicity, regulate the magnitude of $Ca^{2+}$-influx by modulating membrane potential and, in this manner, the driving force for $Ca^{2+}$ entry through other $Ca^{2+}$-permeable pathways, and are not regulated by a voltage or $Ca^{2+}$-dependent inactivation. The invention further relates to the use of recombinant nucleic acids that encode TRPM4b and the methods of utilizing TRPM4b to bind candidate bioactive agents, for modulating TRPM4b activity, and for measuring TRPM4b permeability to monovalent cations. The invention further relates to methods of modulating the cellular expression of the nucleic acids that encode TRPM4b.

One embodiment of the invention provides methods for screening for candidate bioactive agents that bind to TRPM4b. In this method, TRPM4b, or a fragment thereof, is contacted with a candidate agent, and it is determined whether the candidate agent binds to TRPM4b. An embodiment of the invention provides for contacting TRPM4b with a library of two or more candidate agents and then determining the binding of one or more of the candidate agents to TRPM4b. In a preferred embodiment, $Ca^{2+}$ may be present in combination with one or more candidate agents.

In a further embodiment, TRPM4b comprises an ion channel and the candidate agent(s) that bind the TRPM4b channel modulate the monovalent cationic permeability of the TRPM4b channel. In some embodiments, the candidate agent(s) that bind TRPM4b, open the TRPM4b channel. In other embodiments, the candidate agents that bind TRPM4b, close the TRPM4b channel. In still other embodiments of the invention, the monovalent cations which permeate TRPM4b include $Na^+$, $K^+$, and $Cs^+$.

In some embodiments the TRPM4b channel is in a recombinant cell which comprises a recombinant nucleic acid encoding TRPM4b, an inducible promoter which is operably linked to the recombinant nucleic acid, and a monovalent cation indicator, such as fura-2. The recombinant cell is induced to express TRPM4b and it is then contacted with a monovalent cation and a candidate agent. In another embodiment, the recombinant cell is contacted with a candidate agent prior to being contacted with a monovalent cation. Intracellular levels of the monovalent cation are detected using the monovalent cation indicator. An embodiment of the invention provides for contacting the recombinant cell with a monovalent cation solution comprising $Na^+$, $K^+$, and $Cs^+$. In some embodiments, the candidate agent increases the monovalent cation permeability of the TRPM4b channel. In other embodiments, the candidate agent decreases the monovalent cation permeability of the TRPM4b channel. In a preferred embodiment, the candidate agent alters the membrane potential of the recombinant cell by either increasing or decreasing monovalent cation permeability of the TRPM4b channel. In another preferred embodiment, the monovalent cation indicator comprises a fluorescent molecule. In a more preferable embodiment of the invention, the monovalent cation indicator comprises fura-2. In an alternate embodiment, the production of TRPM4b channel is induced and the intracellular levels of monovalent cation are detected in the presence of a candidate agent. That level is compared to the intracellular level of monovalent cation detected in an uninduced recombinant cell either in the presence or absence of a candidate agent.

It is another object of the invention to provide methods for measuring the monovalent ion permeability of a TRPM4b channel. In this method, a recombinant cell is provided, which comprises a recombinant nucleic acid encoding TRPM4b, a promoter, either constitutive or inducible, preferably inducible, which is operably linked to the recombinant nucleic acid, and an intracellular cation indicator. The recombinant cell is contacted with a solution comprising a monovalent cation that selectively interacts with the indicator to generate a signal. Intracellular levels of the monovalent cation are then measured when TRPM4b is expressed by detecting the indicator signal. This measurement is compared to endogenous levels in which recombinant TRPM4b is not expressed.

In a broader embodiment, the cell is not limited to a recombinant TRPM4b expressing cell, but may comprise any cell capable of being used with any recombinantly expressed channel protein for determining agents which modulate the activity of the channel. The expression of the recombinant channel is preferably under the control of an inducible promoter.

In a preferred embodiment the monovalent cation indicator comprises a fluorescent molecule such as fura-2. In yet a further embodiment of the invention the monovalent cation which selectively interacts with the cation indicator is $Na^+$, $K^+$, and $Cs^+$. In some embodiments the modulating activity of a candidate bioactive agent which contacts the recombinant cell together with the monovalent cation agent increases the monovalent cation permeability of the TRPM4b channel, in others it decreases it. In a further preferred embodiment, the modulating activity of the candidate agent alters the membrane potential of the recombinant cell by either increasing or decreasing monovalent cation permeability of the TRPM4b channel. In further embodiments the modulating activity of a candidate bioactive agent which contacts the recombinant cell prior to contact with the monovalent cation agent increases the monovalent cation permeability of the TRPM4b channel, in others it decreases it.

It is further an object of the invention to provide methods for screening for candidate bioactive agents that are capable of modulating expression of TRPM4b. In this method, a recombinant cell is provided which is capable of expressing a recombinant nucleic acid encoding TRPM4b, a fragment thereof, including in some embodiments the 5' and/or 3' expression regulation sequences normally associated with the TRPM4b gene. The recombinant cell is contacted with a candidate agent, and the effect of the candidate agent on TRPM4b expression is determined. In some embodiments, the candidate agent may comprise a small molecule, protein, polypeptide, or nucleic acid (e.g., antisense nucleic acid). In another embodiment of the invention, TRPM4b expression levels are determined in the presence of a candidate bioactive agent and these levels are compared to endogenous TRPM4b expression levels. Those candidate agents which regulate TRPM4b expression can be tested in non-recombinant cells to determine if the same effect is reproduced.

BRIEF DESCRIPTION OF THE DRAWINGS

FIG. 1A (SEQ ID NO:2) depicts the schematic and primary structure of TRPM4b with amino-terminal unique region 1-4 (ATU), transmembrane domain regions (TM), coiled-coil region (CC). Underlined amino acids represent the N-terminal extension of TRPM4b; the rest of the sequence is identical to the short splicing variant TRPM4. The amino acid sequence of TRPM4b protein from amino acids 1 through 1214 (SEQ ID NO:2) is also shown. FIG. 1B depicts the Northern blot analysis of RNA from various tissues and human cell lines using a specific TRPM4b antisense RNA probe. Cell lines represent monocytes (U937), B lymphocytes (Ramos), T lymphocytes (Jurkat), basophils (Ku812), melanoma cells (G361) and embryonic kidney cells (HEK-293).

[Ca2+] recorded in inside-out patches excised from TRPM4b-overexpressing HEK-293 cells. The patch was excised into a KCl-based solution in which [Ca2+]i was buffered to 300 nM and the pipette solution was a NaCl-based standard external solution. Channel activity was measured at various membrane potentials as indicated. Data are from a single representative patch out of 17 successful recordings. Note that open probability increases with positive membrane voltage and single-channel amplitudes slightly increase at both positive and negative potentials. (B) Single-channel I-V relationship derived from averages of several events from different patches (n=2-5), yielding a single channel conductance of 25 pS between −60 mV and +60 mV. Note rectification of single-channel amplitudes at positive and negative voltages. (C) Two sample single-channel ramp recordings measured under the conditions as in (A). Ramps spanned −100 to +100 mV and were 5 s long. (D) Cumulative average of 129 single channel ramps (same patch as in (C)), consistent with the behavior of whole-cell currents carried by TRPM4b. Note the characteristic outward rectification and Erev around 0 mV.

Figure 1:
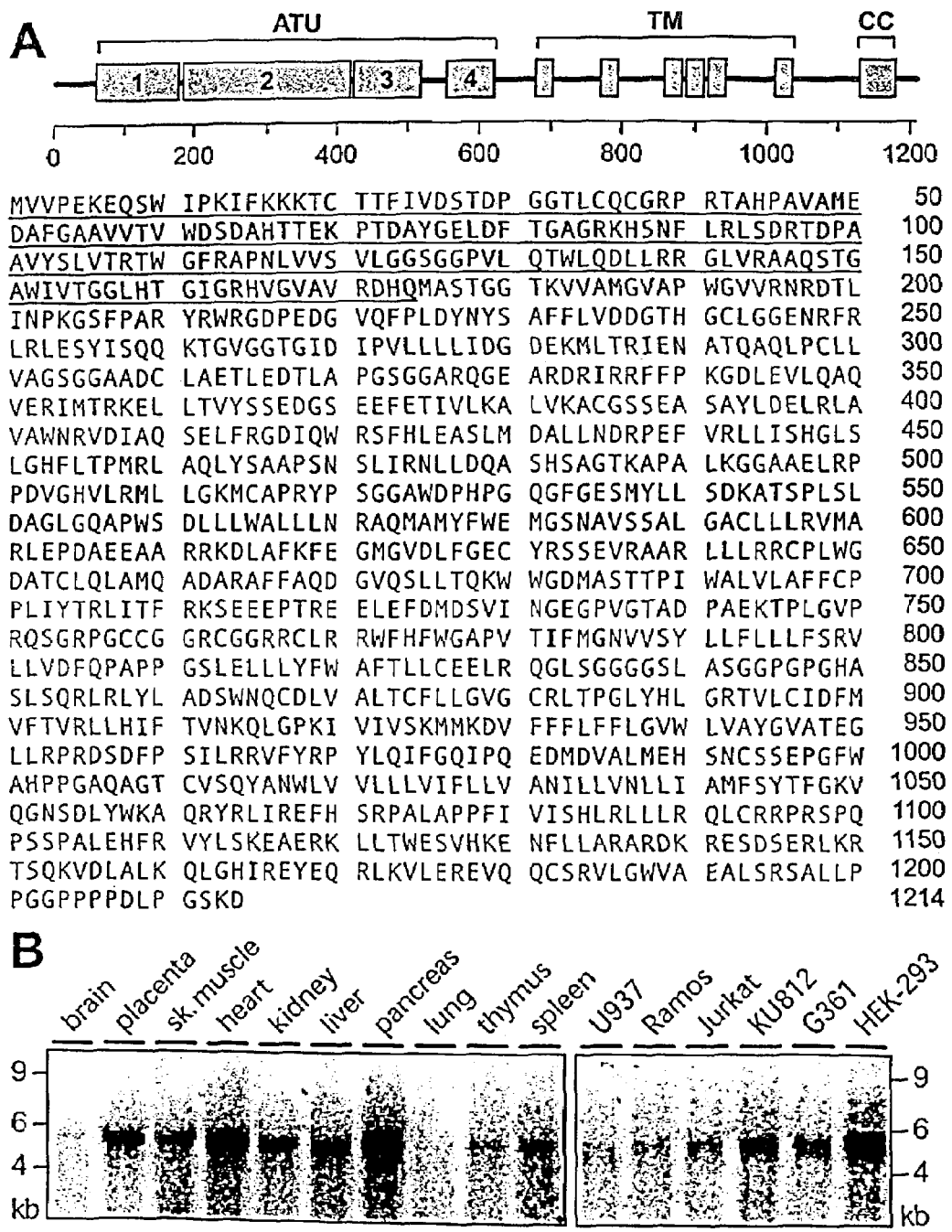
FIGS. 1A-B show the molecular characterization of TRPM4b.
Figure 2:
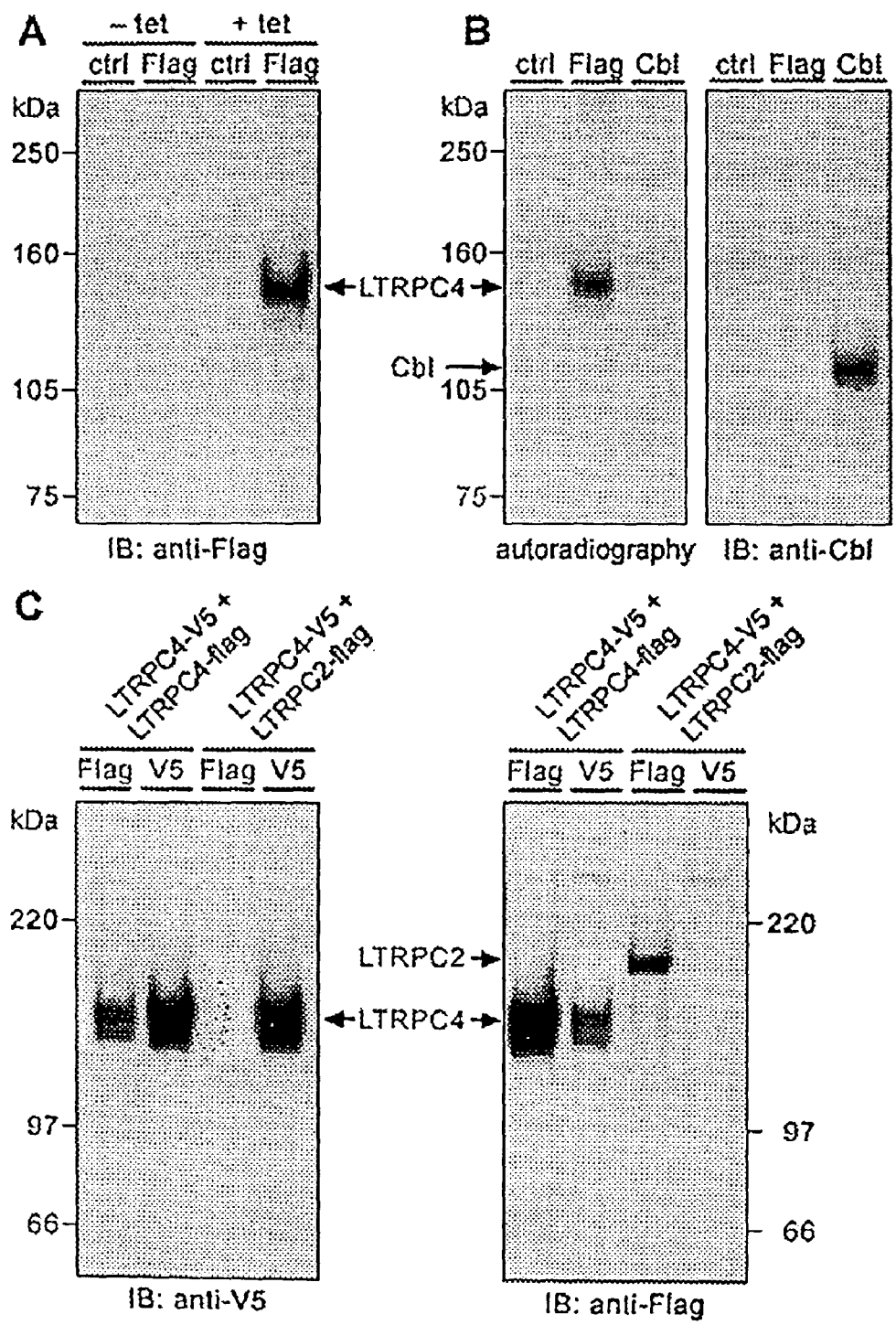
FIGS. 2A-C depict the biochemical analysis of TRPM4b. (A) Tetracycline-inducible expression of TRPM4b. Stable TRPM4b HEK-293 clones were treated or not for 18 hr with 1 mg.ml-1 of tetracycline. Clones were analyzed for expression of a Flag-reactive protein by anti-Flag immunoprecipitation/anti-Flag immunoblotting. Ctrl indicates immunoprecipitation with an irrelevant antibody. (B) Surface expression of TRPM4b. Surface proteins of tetracycline-induced clones were labeled with iodine. TRPM4b was immunoprecipitated with the Flag antibody; the cell viability was tested by immunoprecipitation of the intracytoplasmic protein Cb1. (C) TRPM4b homo-multimerization. HEK-293 cells were co-transfected with two different tagged forms (V5 and Flag) of TRPM4b or co-transfected with TRPM4b V5-tagged and LTRPC2 Flag-tagged. Cell lysates were immunoprecipitated with Flag and V5 and Western blots of the immune complexes were probed with both anti-V5 and anti-Flag antibodies.
Figure 3:
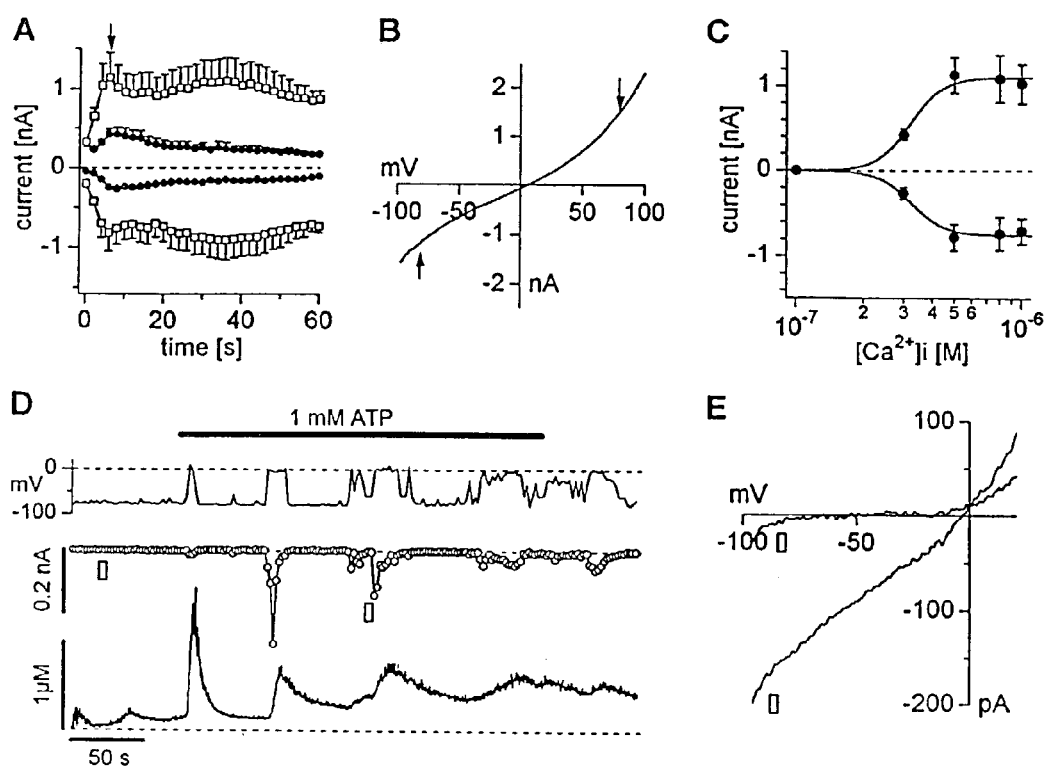
FIGS. 3A-E depict the functional expression of TRPM4b in HEK-293 cells. (A) Whole-cell recordings in HEK-293 cells overexpressing TRPM4b. Average inward and outward currents carried by TRPM4b at −80 and +80 mV, respectively. Cells were perfused with solutions in which [Ca2+]i clamped to either 300 nM (closed circles, n=5±s.e.m.) or 500 nM (open squares, n=5±s.e.m). Arrow indicates the time at which the raw data trace displayed in (B) was extracted. (B) Current-voltage relationship under experimental conditions as in (A), obtained 8 s after whole-cell establishment from a representative cell perfused with 500 nM [Ca2+]i. Arrows indicate −80 and +80 mV, respectively. (C) Dose-response behavior of expressed TRPM4b to various intracellular calcium concentrations. Data points represent average inward and outward currents at −80 and +80 mV, respectively, taken 8 s after whole-cell establishment (n=3-5). (D) Receptor-mediated activation of expressed TRPM4b. Shown are concomitant measurements of global [Ca2+]i (bottom trace), whole-cell current (middle trace) and reversal potential (Erev) (top trace) in a representative cell (total n=8). For the time indicated, the cell was superfused with an extracellular solution containing 1 mM ATP. Holding potential was −60 mV to promote calcium influx. Note that TRPM4b current amplitude does not strictly follow changes in [Ca2+]i and the initial release transient is less effective at activating TRPM4b than the later phase of calcium influx. Symbols Å and Å indicate the time at which raw data traces displayed in (E) were extracted. (E) Current-voltage relationships from the same cell as shown in (D). Both a control current trace before ATP challenge and a TRPM4b current trace (214 s after whole-cell establishment) are displayed.
Figure 4:
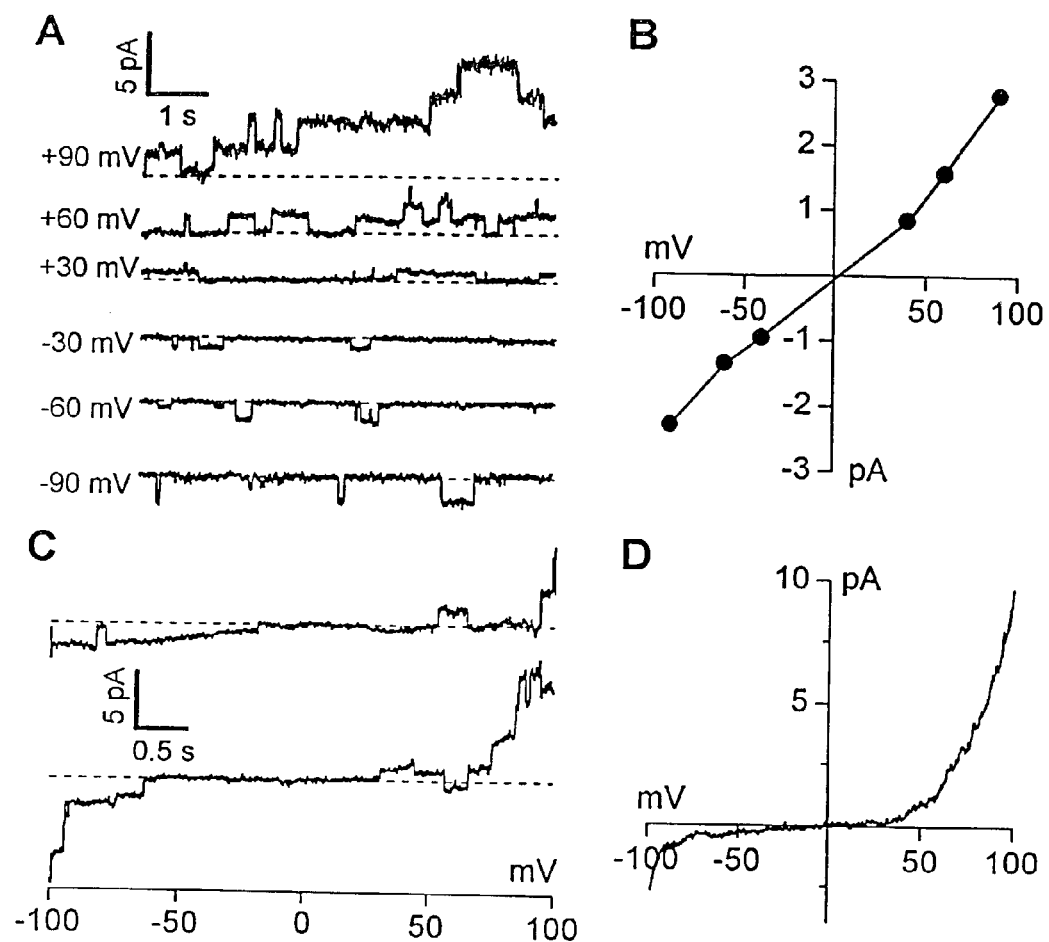
FIGS. 4A-D depict the single channel properties of TRPM4b. (A) Activation of TRPM4b channels by 300 nM
Figure 5:
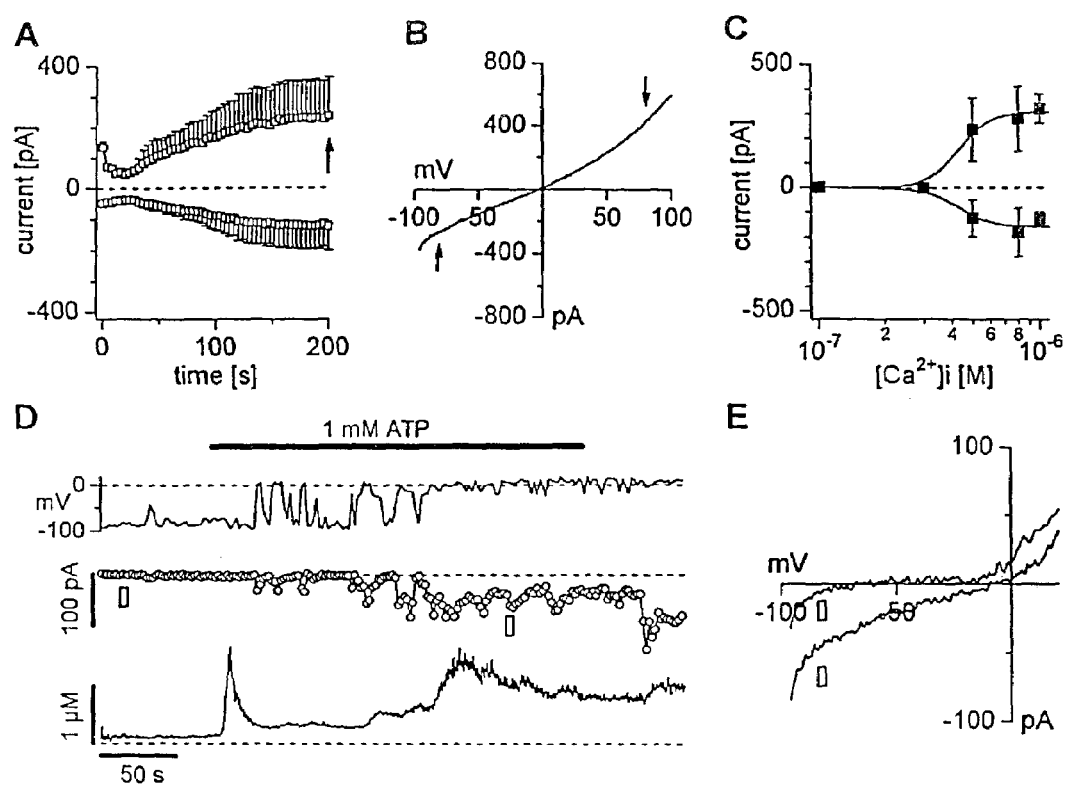

FIGS. 5A-E depict endogenous TRPM4b in HEK-293 cells. (A) Whole-cell recordings in wild-type HEK-293 cells perfused with solutions in which [Ca2+]i clamped to 500 nM (n=3±s.e.m). Average inward and outward currents at −80 and +80 mV, respectively, carried by endogenous currents with TRPM4b characteristics. Arrow indicates the time at which the raw data trace displayed in (B) was extracted. Note that activation of endogenous TRPM4b proceeds slightly slower than overexpressed recombinant TRPM4b. (B) Current-voltage relationship under experimental conditions as in (A), obtained from a representative cell 200 s after whole-cell establishment. Arrows indicate −80 and +80 mV, respectively. (C) Dose-response behavior of expressed TRPM4b to various intracellular calcium concentrations. Data points represent average inward and outward currents at −80 and +80 mV, respectively, taken 200 s after whole-cell establishment (n=3). (D) Receptor-mediated activation of endogenous TRPM4b. Shown are concomitant measurements of global [Ca2+]i (bottom trace), whole-cell current (middle trace) and reversal potential (Erev) (top trace) in a representative cell (total n=8). For the time indicated, the cell was superfused with an extracellular solution containing 1 mM ATP. Holding potential was −60 mV to promote calcium influx. Note the digital behavior of Erev switching between −80 mV and 0 mM in dependence of TRPM4b activation (in a non voltage-clamped cell, the membrane potential will closely follow Erev). Note that TRPM4b current amplitude does not strictly follow changes in [Ca2+]i and the initial release transient is less effective at activating TRPM4b than the later phase of calcium influx. Symbols Á and Á indicate the time at which raw data traces displayed in (E) were extracted. (E) Current-voltage relationships from the same cell as shown in (D). Both a control current trace before ATP challenge and a TRPM4b current trace (286 s after whole-cell establishment) are displayed.

Figure 6:
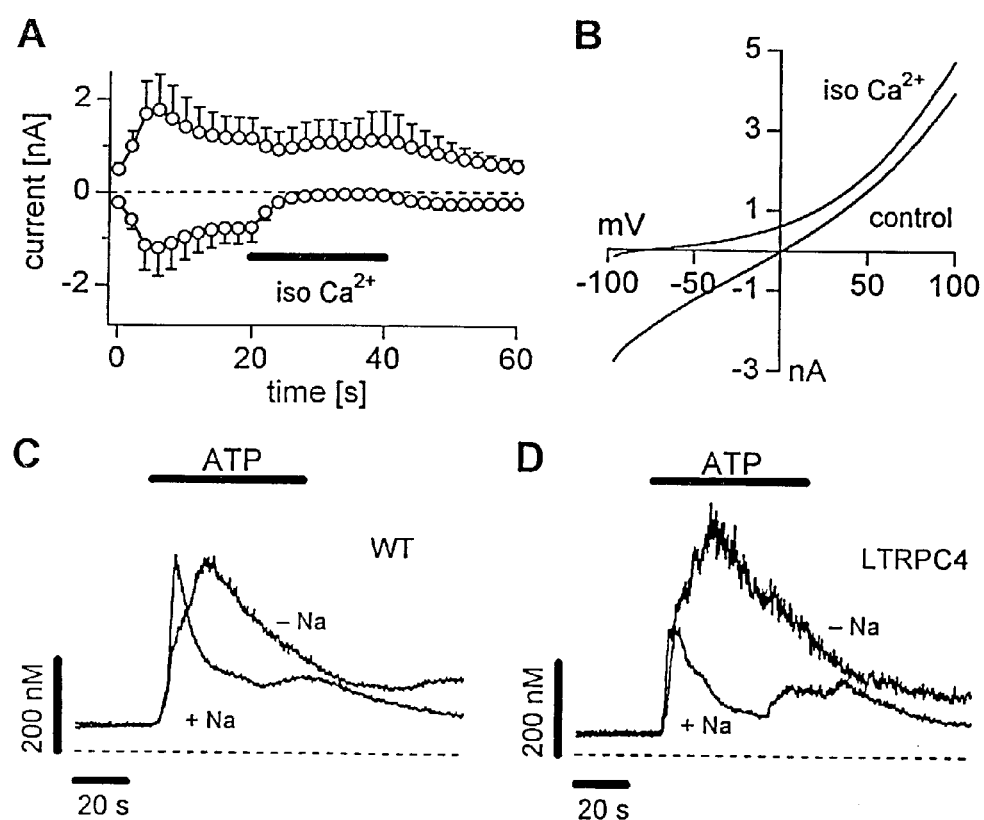

FIGS. 6A-D depict that TRPM4b does not carry Ca2+ and inhibits Ca2+ influx. (A) Whole-cell recordings in HEK-293 cells overexpressing TRPM4b. Average inward and outward currents carried by TRPM4b at −80 and +80 mV, respectively. Cells were perfused with solutions in which [Ca2+]i was buffered to 800 nM (n=5±s.e.m.). Cells were exposed to 120 mM isotone CaCl2 as indicated by the black bar (300 mOsm). Note that inward currents are completely suppressed, suggesting that TRPM4b does not carry Ca2+ ions. (B) Current-voltage relationships of TRPM4b currents under experimental conditions as in (A) measured just before and during application of isotone CaCl2 (40 s after whole-cell establishment). Note that isotone CaCl2 application changes Erev to −80 mV and outward K+ currents remain largely unaffected. (C) Averaged [Ca2+]i signals in intact WT HEK-293 cells loaded with, fura-2-AM and stimulated by the purinergic receptor agonist ATP (n=7-10). During the time indicated by the bar, cells were exposed to 1 mM ATP in either Na+-based (+Na) or choline-based (−Na) extracellular solutions, as indicated by labels. (D) Same experimental protocol as in (C), except that the measurements were performed on TRPM4b-overexpressing HEK-293 cells (n=8-11).

FIG. 7 shows the recombinant nucleic acid molecule of a TRPM4b cDNA comprised of nucleic acid sequences from 1 through about 4061 (SEQ ID NO:1).

FIG. 8 shows the amino acid sequence of a recombinant TRPM4b protein comprised of sequences from 1 through about 1214 (SEQ ID NO:2).

DETAILED DESCRIPTION OF THE PREFERRED EMBODIMENTS

The invention relates, in part, to methods useful in identifying molecules, that bind TRPM4b, which modulate TRPM4b ion channel activity, and/or which alter expression of TRPM4b within cells. The TRPM4b channels as described herein comprise TRPM4b polypeptides, which are in turn encoded by TRPM4b nucleic acids. The ion channels described herein are preferably formed in HEK-293 cells and comprise one or more novel TRPM4b polypeptides, which exhibit one or more of the unique TRPM4b properties described herein.

As described herein, the term "TRPM4b" refers to a member of the novel family of $Ca^{2+}$ regulated transmembrane channel polypeptides. The polypeptides are also defined by their amino acid sequence, the nucleic acids which encode them, and the novel properties of TRPM4b. Such novel properties include specific activation by elevations in cytoplasmic $Ca^{2+}$ in the nanomolar range, direct gating by $Ca^{2+}$, conduction of monovalent cations such as $Na^+$, $K^+$, and $Cs^+$ without significant $Ca^{2+}$ permeation, activation subsequent to receptor-mediated $Ca^{2+}$-mobilization, support of important cellular responses such as neuronal bursting activity, kidney cell osmotic regulation and/or cardiac rhythmicity, regulation of $Ca^{2+}$-influxes by modulation of membrane potential and, in this manner, the driving force for $Ca^{2+}$ entry through other $Ca^{2+}$-permeable pathways, and an absence of regulation by a voltage or $Ca^{2+}$-dependent inactivation. Direct gating of the TRPM4b channel by $Ca^{2+}$ appears to begin when $Ca^{2+}$ concentrations are within the 300 nM range.

The TRPM4b polypeptides and channels are fundamentally distinct from th-e "SOC" (Store Operated Channels) and "CRAC" (Calcium Release Activated Channels) polypeptides and channels, disclosed in "Characterization of a Calcium Family," WO 00/40614, the disclosure of which is expressly incorporated herein by reference. The SOC and CRAC proteins "may be activated upon depletion of $Ca^{2+}$ from intracellular calcium stores" (see WO 00/40614 at page 2) and are further "subject to inhibition by high levels of intracellular calcium" (see WO 00/40614 at page 10). The TRPM4b channels of the invention, conversely, exhibit enhanced activity in the presence of high intracellular levels of calcium, may be directly gated by cytosolic $Ca^{2+}$ concentrations in the nanomolar range, decrease the driving force for $Ca^{2+}$ influx through store operated $Ca^{2+}$ channels of non-excitable cells, are not influenced by depletion or reduction of intracellular calcium stores, and operate to depolarize cell membranes in a $Ca^{2+}$-dependent manner. SOC and CRAC are not regulated in this manner.

The TRPM4b polypeptide is a novel member of the LTRPC family. The specific sequence disclosed herein as SEQ ID NO:2 (FIG. 8) was derived from human kidney cells. However, TRPM4b is believed to be broadly expressed in various mammalian tissues, and is widely expressed in human tissues, with a dominant expression in the heart, placenta, and pancreas, as well as in the cell lines of the human hematopoetic system.

TRPM4b can be derived from natural sources or recombinantly modified to make TRPM4b variants. The term "TRPM4b sequence" specifically encompasses naturally-occurring truncated or secreted forms (e.g., an extracellular domain sequence), naturally-occurring variant forms (e.g., alternatively spliced forms) and naturally-occurring allelic variants. The native sequence of the TRPM4b polypeptide from human kidney cells is a full-length or mature native sequence TRPM4b polypeptide comprising amino acids from 1 through about 1214 of SEQ ID NO:2 (FIG. 8).

The TRPM4b polypeptide of the invention, or a fragment thereof, also includes polypeptides having at least about 80% amino acid sequence identity, more preferably at least about 85% amino acid sequence identity, even more preferably at least about 90% amino acid sequence identity, and most preferably at least about 95% sequence identity with the amino acid sequence of SEQ ID NO:2. Such TRPM4b polypeptides include, for instance, TRPM4b polypeptides wherein one or more amino acid residues are substituted and/or deleted, at the N- or C-terminus, as well as within one or more internal domains, of the sequence of SEQ ID NO:2. Those skilled in the art will appreciate that amino acid changes may alter post-translational processes of the TRPM4b polypeptide variant, such as changing the number or position of glycosylation sites or altering the membrane anchoring characteristics. All TRPM4b proteins, however, exhibit one or more of the novel properties of the TRPM4b polypeptides as defined herein.

"Percent (%) amino acid sequence identity" with respect to the TRPM4b polypeptide sequences identified herein is defined as the percentage of amino acid residues in a candidate sequence that are identical with the amino acid residues of SEQ ID NO:2 (FIG. 8), after aligning the sequences and introducing gaps, if necessary, to achieve the maximum percent sequence identity, and not considering any conservative substitutions as part of the sequence identity. The % identity values used herein are generated by WU-BLAST-2 which was obtained from Altschul et al., *Methods in Enzymology*, 266:460-480 (1996); http://blast.wustl/edu/blast/README-.html. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a further embodiment, the % identity values used herein are generated using a PILEUP algorithm. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351-360 (1987); the method is similar to that described by Higgins & Sharp *CABIOS* 5:151-153 (1989). Useful PILEUP parameters including a default gap weight of 3.00, a default gap length weight of 0.10, and weighted end gaps.

In yet another embodiment, TRPM4b polypeptides from humans or from other organisms may be identified and isolated using oligonucleotide probes or degenerate polymerase chain reaction (PCR) primer sequences with an appropriate genomic or cDNA library. As will be appreciated by those in the art, the TRPM4b unique nucleic acid sequence comprising nucleotide sequences of SEQ ID NO:1 (FIG. 7) encoding amino acids 1-174 of SEQ ID NO:2 (FIG. 8) or portions thereof, is particularly useful as a probe and/or PCR primer sequence. As is generally known in the art, preferred PCR primers are from about 15 to about 35 nucleotides in length, with from about 20 to about 30 being preferred, and may contain inosine as needed. The conditions for the PCR reaction are well known in the art.

In a preferred embodiment, TRPM4b is a "recombinant protein" which is made using recombinant techniques, i.e. through the expression of a recombinant TRPM4b nucleic acid. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or of amino acid substitutions, additions and deletions, as discussed below.

In a further embodiment, TRPM4b variants may be recombinantly engineered by replacing one amino acid with another amino acid having similar structural and/or chemical properties, such as the replacement of a leucine with a serine, i.e., conservative amino acid replacements.

In a further embodiment substitutions, deletions, additions or any combination thereof may be used to make TRPM4b variants. Generally these changes are done on a few amino acids to minimize the alteration of the molecule. However, larger changes may be tolerated in certain circumstances. When small alterations in the characteristics of the TRPM4b polypeptide are desired, substitutions are generally made in accordance with the following Table 1:

TABLE 1

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

In a further embodiment, substantial changes in function or in immunological identity are made by selecting substitutions that are less conservative than those shown in Chart 1. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine. The TRPM4b variants of this embodiment exhibit one or more properties of the TRPM4b polypeptides originally defined herein.

In a further emodiment, the variants typically exhibit the same qualitative biological activity and will elicit the same immune response as the naturally-occurring analogue, although variants also are selected to modify the characteristics of the TRPM4b polypeptides as needed. Alternatively, the variant may be designed such that the biological activity of the TRPM4b polypeptides is altered. For example, glycosylation sites may be altered or removed. The proteins enocoded by the nucleic acid variants exhibit at least one of the novel TRPM4b polypeptide properties defined herein.

The proteins enocoded by nucleic acid variants exhibit at least one of the novel TRPM4b polypeptide properties defined herein.

As used herein, "TRPM4b nucleic acids" or their grammatical equivalents, refer to nucleic acids, that encode TRPM4b polypeptides exhibiting one or more of the novel TRPM4b polypeptide properties previously described. The TRPM4b nucleic acids exhibit sequence homology to SEQ ID NO:1 (FIG. 7) where homology is determined by comparing sequences or by hybridization assays.

A TRPM4b nucleic acid encoding a TRPM4b polypeptide is homologous to the cDNA forth in FIG. 7 (SEQ ID NO:1). Such TRPM4b nucleic acids are preferably greater than about 75% homologous, more preferably greater than about 80%, more preferably greater than about 85% and most preferably greater than 90% homologous. In some embodiments the homology will be as high as about 93 to 95 or 98%. Homology in this context means sequence similarity or identity, with identity being preferred. A preferred comparison for homology purposes is to compare the sequence containing sequencing differences to the known TRPM4b sequence. This homology will be determined using standard techniques known in the art, including, but not limited to, the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *PNAS USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387-395 (1984), preferably using the default settings, or by inspection.

In a preferred embodiment, the % identity values used herein are generated using a PILEUP algorithm. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351-360 (1987); the method is similar to that described by Higgins & Sharp CABIOS 5:151-153 (1989). Useful PILEUP parameters including a default gap weight of 3.00, a default gap length weight of 0.10, and weighted end gaps.

In preferred embodiment, a BLAST algorithm is used. BLAST is described in Altschul et al., *J. Mol. Biol.* 215:403-410, (1990) and Karlin et al., *PNAS USA* 90:5873-5787 (1993). A particularly useful BLAST program is the WU-BLAST-2, obtained from Altschul et al., *Methods in Enzymology,* 266:460-480 (1996); http://blast.wustl/edu/blast/README.html. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a preferred embodiment, "percent (%) nucleic acid sequence identity" is defined as the percentage of nucleotide residues in a candidate sequence that are identical with the nucleotide residue sequences of SEQ ID NO:1 (FIG. 7). A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer nucleosides than those of SEQ ID NO:1 (FIG. 7), it is understood that the percentage of homology will be determined based on the number of homologous nucleosides in relation to the total number of nucleosides. Thus, for example, homology of sequences shorter than those of the sequences identified herein and as discussed below, will be determined using the number of nucleosides in the shorter sequence.

As described above, the TRPM4b nucleic acids can also be defined by homology as determined through hybridization studies. Hybridization is measured under low stringency conditions, more preferably under moderate stringency conditions, and most preferably, under high stringency conditions. The proteins encoded by such homologous nucleic acids exhibit at least one of the novel TRPM4b polypeptide properties defined herein. Thus, for example, nucleic acids which hybridize under high stringency to a nucleic acid having the sequence set forth as SEQ ID NO:1 (FIG. 7) and their complements, are considered TRPM4b nucleic acid sequences providing they encode a protein having a TRPM4b property.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional examples of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like. Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

In another embodiment, less stringent hybridization conditions are used; for example, moderate or low stringency conditions may be used, as are known in the art. For additional details regarding stringency of hybridization reactions, see Ausubel et al., *Current Protocols in Molecular Biology*, Wiley Interscience Publishers, (1995).

The TRPM4b nucleic acids, as defined herein, may be single stranded or double stranded, as specified, or contain portions of both double stranded or single stranded sequence. As will be appreciated by those in the art, the depiction of a single strand ("Watson") also defines the sequence of the other strand ("Crick"); thus the sequences described herein also include the complement of the sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

The TRPM4b nucleic acids, as defined herein, are recombinant nucleic acids. By the term "recombinant nucleic acid" herein is meant nucleic acid, originally formed in vitro, in general, by the manipulation of nucleic acid by polymerases and endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Homologs and alleles of the TRPM4b nucleic acid molecules are included in the definition.

The recombinant cDNA nucleic acid (SEQ ID NO:1) encoding a TRPM4b protein (SEQ ID NO:2), or portions thereof, may be used as hybridization probes for a cDNA library to isolate the full-length TRPM4b gene from other multicellular eukaryotic species, or to isolate still other genes (for instance, those encoding naturally-occurring variants of the TRPM4b polypeptide or the TRPM4b polypeptide from other multicellular eukaryotic species) which have a desired sequence identity to a particular TRPM4b nucleotide coding sequence. Optionally, the length of the probes will be about 20 through about 50 bases. The hybridization probes may be derived from the nucleotide sequences of SEQ ID NO:1 or from genomic sequences including promoters, enhancer elements and introns of particular native nucleotide sequences of TRPM4b. By way of example, a screening method will comprise isolating the coding region of a TRPM4b gene using the known DNA sequence to synthesize a selected probe of about 40 bases.

Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the TRPM4b gene of the invention can be used to screen libraries of human cDNA, genomic DNA or mRNA to determine which members of such libraries the probe hybridizes to. Hybridization have been previously described below.

The probes may also be employed in PCR techniques to generate a pool of sequences for identification of closely related TRPM4b nucleotide coding sequences. Nucleotide sequences encoding TRPM4b polypeptides can also be used to construct hybridization probes for mapping the gene which encodes that TRPM4b and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries In another embodiment, DNA encoding the TRPM4b polypeptide may be obtained from a cDNA library prepared from tissue believed to possess the TRPM4b mRNA and to express it at a detectable level. Accordingly, human TRPM4b DNA can be conveniently obtained from a cDNA library prepared from human tissue, or a cDNA kidney library prepared from human kidney tissue. The TRPM4b-encoding gene may also be obtained from a multicellular eukaryotic genomic library or by oligonucleotide synthesis.

Libraries can be screened with probes (such as antibodies to TRPM4b DNA or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding TRPM4b is to use PCR methodology [Sambrook et al., supra; Dieffenbach et al., *PCR Primer: A Laboratory Manual* (Cold Spring Harbor Laboratory Press, 1995)].

The examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}P$-labeled ADPR, biotinylation or enzyme labeling. Hybridization conditions, including moderate stringency and high stringency, are provided in Sambrook et al., supra, and have been described previously.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, BLAST, BLAST2 and INHERIT which employ various algorithms to measure homology, as has been previously described.

Nucleic acid encoding TRPM4b polypeptides, as defined herein, may be obtained by screening selected cDNA or genomic libraries using all or part of the nucleotide sequences of SEQ ID NO:1 (FIG. 7). Conventional primer extension procedures as described in Sambrook et al., supra, are used to detect precursors and processing intermediates of mRNA that may not have been reverse-transcribed into cDNA.

Nucleotide sequences (or their complement) encoding the TRPM4b polypeptides have various applications in the art of molecular biology, including uses as hybridization probes, in chromosome and gene mapping, and in the generation of anti-sense RNA and DNA.

In another embodiment, the TRPM4b nucleic acids, as defined herein, are useful in a variety of applications, including diagnostic applications, which will detect naturally occurring TRPM4b nucleic acids, as well as screening applications; for example, biochips comprising nucleic acid probes to the TRPM4b nucleic acids sequences can be generated. In the broadest sense, then, by "nucleic acid" or "oligonucleotide" or grammatical equivalents herein means at least two nucleotides covalently linked together.

In another embodiment, the TRPM4b nucleic acid sequence of SEQ ID NO:1 (FIG. 7), as described above, is a cDNA fragment of a larger gene, i.e. it is a nucleic acid segment. "Genes" in this context include coding regions, non-coding regions, and mixtures of coding and non-coding regions. Accordingly, as will be appreciated by those in the art, using the sequences provided herein, additional sequences of TRPM4b genes can be obtained, using techniques well known in the art for cloning either longer sequences or the full length sequences; see Maniatis et al., and Ausubel, et al., supra, hereby expressly incorporated by reference.

Once the TRPM4b nucleic acid, as described above, is identified, it can be cloned and, if necessary, its constituent parts recombined to form the entire TRPM4b gene. Once isolated from its natural source, e.g., contained within a plasmid or other vector or excised therefrom as a linear nucleic acid segment, the recombinant TRPM4b nucleic acid can be further-used as a probe to identify and isolate other TRPM4b nucleic acids, from other multicellular eukaryotic organisms, for example additional coding regions. It can also be used as a "iprecursor" nucleic acid to make modified or variant TRPM4b nucleic acids.

In another embodiment, the TRPM4b nucleic acid (e.g., cDNA or genomic DNA), as described above, encoding the TRPM4b polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

A host cell comprising such a vector is also provided. By way of example, the host cells may be mammalian host cell lines which include Chinese hamster ovary (CHO), COS cells, cells isolated from human bone marrow, human spleen or kidney cells, cells isolated from human cardiac tissue, human pancreatic cells, and human leukocyte and monocyte cells. More specific examples of host cells include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); human pancreatic β-cells; mouse sertoli cells (TM4, Mather, *Biol. Reprod.*, 23:243-251 (1980)); human lung cells (W138, ATCC CCL 75); human liver cells (Hep G2, HB 8065); and mouse mammary tumor cells (MMT 060562, ATCC CCL51). The selection of the appropriate host cell is deemed to be within the skill in the art. In the preferred embodiment, HEK-293 cells are used as host cells. A process for producing TRPM4b polypeptides is further provided and comprises culturing host cells under conditions suitable for expression of the TRPM4b polypeptide and recovering the TRPM4b polypeptide from the cell culture.

In another embodiment, expression and cloning vectors are used which usually contain a promoter, either constitutive or inducible, that is operably linked to the TRPM4b-encoding nucleic acid sequence to direct mRNA synthesis. Promoters recognized by a variety of potential host cells are well known. The transcription of a TRPM4b DNA encoding vector in mammalian host cells is preferably controlled by an inducible promoter, for example, by promoters obtained from heterologous mammalian promoters, e.g., the actin promoter or an immunoglobulin promoter, and from heat-shock promoters. Examples of inducible promoters which can be practiced in the invention include the hsp 70 promoter, used in either single or binary systems and induced by heat shock; the metallothionein promoter, induced by either copper or cadmium (Bonneton et al., FEBS Lett. 1996 380(1-2): 33-38); the *Drosophila* opsin promoter, induced by *Drosophila* retinoids (Picking, et al., Experimental Eye Research. 1997 65(5): 717-27); and the tetracycline-inducible full CMV promoter. Of all the promoters identified, the tetracycline-inducible full CMV promoter is the most preferred. Examples of constitutive promoters include the GAL4 enhancer trap lines in which expression is controlled by specific promoters and enhancers or by local position effects and the transactivator-responsive promoter, derived from *E. coli*, which may be either constitutive or induced, depending on the type of promoter it is operably linked to.

Transcription of a DNA encoding the TRPM4b by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, (α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the TRPM4b coding sequence, but is preferably located at a site 5' from the promoter.

The methods of the invention utilize TRPM4b polypeptides or nucleic acids which encode TRPM4b polypeptides for identifying candidate bioactive agents which bind to TRPM4b, which modulate the activity of TRPM4b ion channels, or which alter the expression of TRPM4b within cells The term "candidate bioactive agent" as used herein describes any molecule which binds to TRPM4b, modulates the activity of a TRPM4b ion channel, and/or alters the expression of TRPM4b within cells. A molecule, as described herein, can be an oligopeptide, small organic molecule, polysaccharide, polynucleotide, or multivalent cation etc. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are multivalent cations or organic molecules, or small organic compounds having a molecular weight of more than 100 and less than about 2,500 daltons (D). Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least-two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the-candidate bioactive agents are naturally occurring proteins or fragments of naturally occurring proteins. Thus, for example, cellular extracts containing proteins, or random or directed digests of proteinaceous cellular extracts, may be used. In this way libraries of multicellular eucaryotic proteins may be made for screening in the methods of the invention. Particularly preferred in this embodiment are libraries of multicellular eukaryotic proteins, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids.

As described above generally for proteins, nucleic acid candidate bioactive agents may be naturally occurring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

In a preferred embodiment, anti-sense RNAs and DNAs can be used as therapeutic agents for blocking the expression of certain TRPM4b genes in vivo. It has already been shown that short antisense oligonucleotides can be imported into cells where they act as inhibitors, despite their low intracellular concentrations caused by their restricted uptake by the cell membrane. (Zamecnik et al., (1986), *Proc. Natl. Acad. Sci. USA* 83:4143-4146). The anti-sense oligonucleotides can be modified to enhance their uptake, e.g. by substituting their negatively charged phosphodiester groups by uncharged groups. In a preferred embodiment, TRPM4b anti-sense RNAs and DNAs can be used to prevent TRPM4b gene transcription into mRNAs, to inhibit translation of TRPM4b mRNAs into proteins, and to block activities of preexisting TRPM4b proteins.

As used herein, a monovalent cation indicator is a molecule that is readily permeable to a cell membrane or otherwise amenable to transport into a cell e.g., via liposomes, etc., and upon entering a cell, exhibits a fluorescence that is either enhanced or quenched upon contact with a monovalent cation. Examples of monovalent cation indicators useful in the invention are set out in Haugland, R. P. *Handbook of Fluorescent Probes and Research Chemicals.*, 6th ed. Molecular Probes, Inc Eugene, Oreg., pp. 504-550 (1996); incorporated herein by reference in its entirety.

In a preferred embodiment for binding assays, either TRPM4b or the candidate bioactive agent is labeled with, for example, a fluorescent, a chemiluminescent, a chemical, or a radioactive signal, to provide a means of detecting the binding of the candidate agent to TRPM4b. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound TRPM4b. As known in the art, unbound labeled streptavidin is removed prior to analysis. Alternatively, TRPM4b can be immobilized or covalently attached to a surface and contacted with a labeled candidate bioactive agent. Alternatively, a library of candidate bioactive agents can be immobilized or covalently attached to a biochip and contacted with a labeled TRPM4b. Procedures which employ biochips are well known in the art.

In a preferred embodiment, the ion permeabilty of TRPM4b is measured in intact cells, preferably HEK-293 cells, which are transformed with a vector comprising nucleic acid encoding TRPM4b and an inducible promoter operably linked thereto. Endogenous levels of intracellular ions are measured prior to inducement and then compared to the levels of intracellular ions measured subsequent to inducement. Fluorescent molecules such as fura-2 can be used to detect intracellular ion levels. TRPM4b permeability to $Na^+$, $K^+$, $Cs^+$ and to other monovalent cations can be measured in this assay.

In a preferred embodiment for screening for candidate bioactive agents which modulate expression levels of TRPM4b within cells, candidate agents can be used which wholly suppress the expression of TRPM4b within cells, thereby altering the cellular phenotype. In a further preferred embodiment, candidate agents can be used which enhance the expression of TRPM4b within cells, thereby altering the cellular phenotype. Examples of these candidate agents include antisense cDNAs and DNAs, regulatory binding proteins and/or nucleic acids, as well as any of the other candidate bioactive agents herein described which modulate transcription or translation of nucleic acids encoding TRPM4b.

In a further embodiment, candidate bioactive agents are used to open TRPM4b channels in a variety of cells such as cells of the nervous, immune, and muscular systems of vertebrates wherein the opening of the TRPM4b channels results in a decreased or reduced immune response in vertebrates. Bioactive agents such as the ones described herein are useful in the treatment of diseases, conditions associated with diseases, or disorders, such autoimmune or graft versus host diseases, or other related autoimmune disorders, wherein the decreased or reduced immune response results in an improved condition of the vertebrate (i.e., the disease, condition associated with the disease, or disorder is prevented, eliminated or diminished).

In still a further embodiment, candidate bioactive agents are used to close TRPM4b channels in a variety of cells such as cells of the nervous, immune, and muscular systems of vertebrates wherein the closing of the TRPM4b channels results in an enhanced or augmented immune response in vertebrates. Bioactive agents such as the ones described herein are useful in the treatment of diseases, conditions associated with diseases, or disorders such as breast and colon cancer, or other forms of cancer, wherein an enhanced or augmented immune response results in the improved condition of the vertebrate (i.e., the disease, condition associated with the disease, or disorder is prevented, eliminated or diminished).

In still another embodiment, the invention provides antibodies which specifically bind to unique epitopes on the TRPM4b polypeptide, e.g., unique epitopes of the protein comprising amino acids from 1 through about 1214 of SEQ ID NO:2 (FIG. 8).

The anti-TRPM4b polypeptide antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the TRPM4b polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The anti-TRPM4b polypeptide antibodies may further comprise monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the TRPM4b polypeptide or a fusion protein thereof Generally, either peripheral blood lymphocytes ("PBLs") are used if cells of human origin are desired, or spleen cells, kidney cells, or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications,* Marcel Dekker, Inc., New York, (1987) pp. 51-63].

The culture medium in which the hybridoma cells are cultured can then be assayed for the presence of monoclonal antibodies directed against a TRPM4b polypeptide. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The anti-TRPM4b polypeptide antibodies may further comprise monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof, particularly, Fab fragments, can be accomplished using routine techniques known in the art.

The anti-TRPM4b polypeptide antibodies may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581(1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by the introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

The anti-TRPM4b polypeptide antibodies, may further comprise heteroconjugate antibodies. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

In a further embodiment, the anti-TRPM4b polypeptide antibodies may have various utilities. For example, anti-TRPM4b polypeptide antibodies may be used in diagnostic assays for TRPM4b polypeptides, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, Monoclonal Antibodies: A Manual of Techniques, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., Nature, 144:945 (1962); David et al., Biochemistry, 13:1014 (1974); Pain et al., J. Immunol Meth., 40:219 (1981); and Nygren, J. Histochem. and Cytochem., 30:407 (1982).

Further, TRPM4b antibodies may be used in the methods of the invention to screen for their ability to modulate the permeability of TRPM4b channels to monovalent cations.

EXAMPLES

Commercially available reagents referred to in the examples were used according to manufacturer's instructions unless otherwise indicated.

Example 1

Cloning and Sequence Analysis of TRPM4b

The genetrapper II solution hybridization method (Life Technologies) was used to isolate the TRPM4b cDNA. Three rounds of screening with three different human cDNA libraries were performed: thirteen PCR-positive colonies were obtained from the kidney library, all containing 3' fragments of the TRPM4b cDNA. Further 5'-sequence was obtained from the spleen library. Using this supplementary 5'-segment to design new fishing oligonucleotides, another 8 PCR positive clones were isolated from a prostate library with one single clone containing the longest ORF, coding for the putative full-length TRPM4b.

Example 2

Northern Blot Analysis

Single-stranded probes were constructed with the NheI/EcoRI/KpnI 1 kb fragment of the human TRPM4b 3'-end. FirstChoice™ Northern Blot for human tissue were obtained from Ambion (Austin, Tex.) and for the cell lines, 3 mg of polyA RNA per lane were used. The dUTP-labeled RNA probe was generated using a T7-directed RNA probe synthesis kit from Ambion. All hybridizations were performed according to the manufacture's protocols.

Example 3

Protein Methods

Full-length TRPM4b cDNA was cloned into a modified version of the pCDNA4/TO vector (Invitrogen) with an N-terminal Flag epitope tag. The correct sequence of the full-length Flag-TRPM4b expression construct was confirmed by DNA sequencing. The Flag-TRPM4b cDNA in pCDNA4/T0 was electroporated into HEK-293 cells previously transfected with the pCDNA6/TR construct for Tet-repressor expression. Cells were placed under zeocin selection, and zeocin-resistant clones were screened for tetracycline-inducible expression of the Flag-tagged TRPM4b protein. Cell surface iodination with Na125I (1 mCi) (Amersham Pharmacia Biotech, Piscataway, N.J.) was carried out by the lactoperoxidase method. For immunoprecipitation, cells (107/ml) were lysed for 30 min at 4° C. in Tris buffer pH 7.5 containing 0.5% Triton X-100 (Bio-Rad, Hercules, Calif.) and proteases inhibitors. The Flag-tagged proteins were immunoprecipitated from cleared lysate by an anti-Flag antibody (Sigma, St. Louis, Mo.). In other experiments, anti-Cb1 antibodies (Santa-Cruz Biotechnology, Santa-Cruz, Calif.) and anti-V5 tag (Invitrogen, Carlsbad, Calif.) were used. The immunoprecipitated proteins were resolved by 6% SDS-PAGE and visualized by Enhanced Chemiluminescence (Amersham Pharmacia Biotech).

Example 4

Cell Culture and Electrophysiology

Wild type and tetracycline-inducible HEK-293 Flag-TRPM4b-expressing cells were cultured at 37° C./5% CO2 in DMEM supplemented with 10% FBS and 2 mM glutamine. The medium was supplemented with blasticidin (5 µg/ml; Invitrogen) and zeocin (0.4 mg/ml; Invitrogen). Cells were resuspended in media containing 1 µg/ml tetracycline (Invitrogen) 24 hours before experiments. For patch-clamp experiments, cells were kept in a standard Ringer's solution (in mM): NaCl 145, KCl 2.8, CaCl2 1, MgCl2 2, glucose 10, Hepes.NaOH 10, pH 7.2. In some experiments, this solution was modified such that all but 1 mM of NaCl was replaced by choline-Cl (choline-based solution). In experiments where ATP was used, it was added at 1 mM of the Mg2+ salt and extracellular Ca2+ concentration was raised to 2 mM. The standard pipette-filling solutions contained (in mM): K-glutamate 145, NaCl 8, MgCl2 1, Cs-BAPTA 10, pH 7.2 adjusted with KOH. In some experiments, [Ca2+]i was buffered to 0.1-1 µM by 10 mM BAPTA and appropriate concentrations of CaCl2 or left unbuffered. For inside-out single-channel recordings, the patch was excised into a similar solution, except that KCl was used instead of K-glutamate. All reagents were purchased from Sigma and dissolved in the standard intracellular solution. Patch-clamp experiments were performed in the whole-cell configuration at 21-25° C. Data was acquired with "Pulse" software controlling an EPC-9 amplifier (HEKA, Lambrecht, Germany). Voltage ramps of 50 ms duration spanning the voltage range of −100 to +100 mV were delivered from a holding potential of 0 mV at a rate of 0.5 Hz over a period of 200 to 400 seconds. When applicable, voltages were corrected for liquid junction potentials. Currents were filtered at 2.9 kHz and digitized at 100 its intervals. Capacitive currents and series resistance were determined and corrected before each voltage ramp. For analysis, the very first ramps prior to current activation were digitally filtered at 2 kHz, pooled and used for leak-subtraction of all subsequent current records. The low-resolution temporal development of currents at a given potential was extracted from the leak-corrected individual ramp current records by measuring the current amplitudes at voltages of −80 mV or +80 mV. Single-channel recordings were performed in the inside-out configuration and currents were filtered and sampled as above. For display purposes, data records were digitally filtered and down-sampled to 100 Hz.

Example 5

Calcium Measurements

The cytosolic calcium concentration of individual patch-clamped or intact cells was monitored at a rate of 5 Hz with a photomultiplier-based system using a monochromatic light source tuned to excite fura-2 fluorescence at 360 and 390 nm for 20 ms each. Emission was detected at 450-550 nm with a photomultiplier, whose analog signals were sampled and processed by X-Chart software (HEKA, Lambrecht, Germany). Fluorescence ratios were translated into free intracellular calcium concentration based on calibration parameters derived from patch-clamp experiments with calibrated calcium concentrations. In patch-clamp experiments, fura-2 was added to the standard intracellular solution at 100 µM. Ester loading of intact cells was performed by incubating cells for 30-45 min in standard solution supplemented with 5 µM fura-2-AM. Local perfusion of individual cells with ATP was achieved through a wide-tipped, pressure-controlled application pipette (3 µm diameter) placed at a distance of 30 µm from the cell under investigation.

What is claimed is:

1. A method for screening for a candidate bioactive agent capable of modulating the monovalent cationic permeability of a recombinant TRPM4b channel, wherein said TRPM4b channel is capable of being activated with calcium in the nanomolar range and wherein said TRPM4b channel is permeable to monovalent cations selected from the group consisting of $Na^+$, $K^+$ and $Cs^+$ without significant calcium permeation, said method comprising the steps of:

a) activating a recombinant TRPM4b channel;
   b) contacting said recombinant TRPM4b channel with a candidate bioactive agents,
   c) measuring the monovalent cationic permeability of said recombinant TRPM4b channel after said contacting with said candidate bioactive agent;
   d) comparing said monovalent cationic permeability of said recombinant TRPM4b channel after said contacting with said candidate bioactive agent with the cationic permeability of said recombinant TRPM4b channel in the absence of said candidate bioactive agent to determine whether said bioactive candidate agent modulates the monovalent cationic permeability of said recombinant TRPM4b channel.

2. The method of claim 1 wherein said monovalent cationic permeability of said recombinant TRPM4b channel is increased after said contacting with said bioactive candidate agent.

3. The method of claim 1 wherein said monovalent cationic permeability of said recombinant TRPM4b channel is decreased after said contacting with said bioactive candidate agent.

4. The method of claim 1, wherein said recombinant TRPM4b channel is present in HEK-293 cells.

5. The method of claim 1, wherein said recombinant TRPM4b channel is present in a membrane patch.

* * * * *

SEQUENCE LISTING

<160> NUMBER OF SEQ ID NOS: 2

<210> SEQ ID NO 1
<211> LENGTH: 4061
<212> TYPE: DNA

<213> ORGANISM: Homo sapiens

<400> SEQUENCE: 1

```
ggtctggaag cagagccggc ggagggagcg ccggggccct gggctgcagg aggttgcggc    60
ggccgcggca gcatggtggt gccggagaag gagcagagct ggatcccaa gatcttcaag   120
aagaagacct gcacgacgtt catagttgac tccacagatc cgggagggac cttgtgccag   180
tgtgggcgcc cccggaccgc ccaccccgca gtggccatgg aggatgcctt cggggcagcc   240
gtggtgaccg tgtgggacag cgatgcacac accacggaga agcccaccga tgcctacgga   300
gagctggact tcacggggc cggccgcaag cacagcaatt cctccggct ctctgaccga   360
acggatccag ctgcagttta tagtctggtc acacgcacat ggggcttccg tgccccgaac   420
ctggtggtgt cagtgctggg gggatcgggg ggccccgtcc tccagacctg gctgcaggac   480
ctgctgcgtc gtgggctggt gcgggctgcc cagagcacag gagcctggat tgtcactggg   540
ggtctgcaca cggcatcgg ccggcatgtt ggtgtggctg tacgggacca tcagatggcc   600
agcactgggg gcaccaaggt ggtggccatg ggtgtggccc cctggggtgt ggtccggaat   660
agagacaccc tcatcaaccc caagggctcg ttccctgcga gtaccggtg gcgcggtgac   720
ccggaggacg gggtccagtt tcccctggac tacaactact cggccttctt cctggtggac   780
gacggcacac acggctgcct ggggggcgag aaccgcttcc gcttgcgcct ggagtcctac   840
atctcacagc agaagacggg cgtgggaggg actggaattg acatccctgt cctgctcctc   900
ctgattgatg tgatgagaa gatgttgacg cgaatagaga acgccaccca ggctcagctc   960
ccatgtctcc tcgtggctgg ctcaggggga gctgcggact gcctggcgga gaccctggaa  1020
gacactctgg ccccagggag tggggagcc aggcaaggcg aagcccgaga tcgaatcagg  1080
cgtttctttc ccaaagggga ccttgaggtc ctgcaggccc aggtggagag gattatgacc  1140
cggaaggagc tcctgacagt ctattcttct gaggatgggt ctgaggaatt cgagaccata  1200
gttttgaagg cccttgtgaa ggcctgtggg agctcggagg cctcagccta cctggatgag  1260
ctgcgtttgg ctgtggcttg gaaccgcgtg gacattgccc agagtgaact ctttcggggg  1320
gacatccaat ggcggtcctt ccatctcgaa gcttccctca tggacgccct gctgaatgac  1380
cggcctgagt tcgtgcgctt gctcattcc acggcctca gctgggcca ttcctgacc  1440
ccgatgcgcc tggcccaact ctacagcgcg gcgccctcca actcgctcat ccgcaacctt  1500
ttggaccagg cgtcccacag cgcaggcacc aaagccccag ccctaaaagg gggagctgcg  1560
gagctccggc cccctgacgt gggcatgtg ctgaggatgc tgctgggaa gatgtgcgcg  1620
ccgaggtacc cctccggggg cgcctggac cctcacccag ccagggctt cggggagagc  1680
atgtatctgc tctcggacaa ggccaccctg ccgctctcgc tggatgctgg cctcgggcag  1740
gccccctgga gcgacctgct ctttgggca ctgttgctga acagggcaca gatggccatg  1800
tacttctggg agatgggttc caatgcagtt tcctcagctc ttggggcctg tttgctgctc  1860
cgggtgatgg cacgcctgga gcctgacgct gaggaggcag cacggaggaa agacctggcg  1920
ttcaagtttg aggggatggg cgttgacctc tttggcgagt gctatcgcag cagtgaggtg  1980
agggctgccc gcctcctcct ccgtcgctgc ccgctctggg gggatgccac ttgcctccag  2040
ctggccatgc aagctgacgc ccgtgccttc tttgcccagg atggggtaca gtctctgctg  2100
acacagaagt ggtggggaga tatggccagc actacaccca tctgggccct ggttctcgcc  2160
ttcttttgcc ctccactcat ctacacccgc ctcatcacct tcaggaaatc agaagaggag  2220
cccacacggg aggagctaga gtttgacatg gatagtgtca ttaatgggga agggcctgtc  2280
```

-continued

```
gggacggcgg acccagccga agaagacgccg ctgggggtcc cgcgccagtc gggccgtccg    2340
ggttgctgcg ggggccgctg cggggggcgc cggtgcctac gccgctggtt ccacttctgg    2400
ggcgcgccgg tgaccatctt catgggcaac gtggtcagct acctgctgtt cctgctgctt    2460
ttctcgcggg tgctgctcgt ggatttccag ccggcgccgc ccggctccct ggagctgctg    2520
ctctatttct gggcttttcac gctgctgtgc gaggaactgc gccagggcct gagcggaggc    2580
gggggcagcc tcgccagcgg ggcccccggg cctggccatg cctcactgag ccagcgcctg    2640
cgcctctacc tcgccgacag ctggaaccag tgcgacctag tggctctcac ctgcttcctc    2700
ctgggcgtgg gctgccggct gaccccgggt ttgtaccacc tgggccgcac tgtcctctgc    2760
atcgacttca tggttttcac ggtgcggctg cttcacatct tcacggtcaa caaacagctg    2820
gggcccaaga tcgtcatcgt gagcaagatg atgaaggacg tgttcttctt cctcttcttc    2880
ctcggcgtgt ggctggtagc ctatggcgtg ccacggagg ggctcctgag gccacgggac    2940
agtgacttcc caagtatcct gcgccgcgtc ttctaccgtc cctacctgca gatcttcggg    3000
cagattcccc aggaggacat ggacgtggcc ctcatggagc acagcaactg ctcgtcggag    3060
cccggcttct gggcacaccc tcctgggggcc caggcgggca cctgcgtctc ccagtatgcc    3120
aactggctgg tggtgctgct cctcgtcatc ttcctgctcg tggccaacat cctgctggtc    3180
aacttgctca ttgccatgtt cagttacaca ttcggcaaag tacagggcaa cagcgatctc    3240
tactggaagg cgcagcgtta ccgcctcatc cgggaattcc actctcggcc cgcgctggcc    3300
ccgcccttta tcgtcatctc ccacttgcgc ctcctgctca ggcaattgtg caggcgaccc    3360
cggagccccc agccgtcctc cccggccctc gagcatttcc gggtttacct ttctaaggaa    3420
gccgagcgga agctgctaac gtgggaatcg gtgcataagg agaactttct gctggcacgc    3480
gctagggaca gcgggagag cgactccgag cgtctgaagc gcacgtccca gaaggtggac    3540
ttggcactga aacagctggg acacatccgc gagtacgaac agcgcctgaa agtgctggag    3600
cgggaggtcc agcagtgtag ccgcgtcctg gggtgggtgg ccgaggccct gagccgctct    3660
gccttgctgc ccccaggtgg gccgccaccc cctgacctgc ctgggtccaa agactgagcc    3720
ctgctggcgg acttcaagga aagcccccca caggggattt tgctcctaga gtaaggctca    3780
tctgggcctc ggccccgca cctggtggcc ttgtccttga ggtgagcccc atgtccatct    3840
gggccactgt caggaccacc tttgggagtg tcatccttac aaaccacagc atgcccggct    3900
cctcccagaa ccagtcccag cctggagga tcaaggcctg gatcccgggc cgttatccat    3960
ctggaggctg cagggtcctt ggggtaacag ggaccacaga ccccctcacca ctcacagatt    4020
cctcacactg gggaaataaa gccatttcag aggaaaaaaa a                       4061
```

<210> SEQ ID NO 2
<211> LENGTH: 1214
<212> TYPE: PRT
<213> ORGANISM: Homo sapiens

<400> SEQUENCE: 2

```
Met Val Val Pro Glu Lys Glu Gln Ser Trp Ile Pro Lys Ile Phe Lys
 1               5                  10                  15

Lys Lys Thr Cys Thr Thr Phe Ile Val Asp Ser Thr Asp Pro Gly Gly
            20                  25                  30

Thr Leu Cys Gln Cys Gly Arg Pro Arg Thr Ala His Pro Ala Val Ala
        35                  40                  45

Met Glu Asp Ala Phe Gly Ala Ala Val Val Thr Val Trp Asp Ser Asp
```

```
                50                  55                  60
Ala His Thr Thr Glu Lys Pro Thr Asp Ala Tyr Gly Glu Leu Asp Phe
65                  70                  75                  80

Thr Gly Ala Gly Arg Lys His Ser Asn Phe Leu Arg Leu Ser Asp Arg
                85                  90                  95

Thr Asp Pro Ala Ala Val Tyr Ser Leu Val Thr Arg Thr Trp Gly Phe
            100                 105                 110

Arg Ala Pro Asn Leu Val Val Ser Val Leu Gly Gly Ser Gly Gly Pro
        115                 120                 125

Val Leu Gln Thr Trp Leu Gln Asp Leu Leu Arg Arg Gly Leu Val Arg
    130                 135                 140

Ala Ala Gln Ser Thr Gly Ala Trp Ile Val Thr Gly Leu His Thr
145                 150                 155                 160

Gly Ile Gly Arg His Val Gly Val Ala Val Arg Asp His Gln Met Ala
                165                 170                 175

Ser Thr Gly Gly Thr Lys Val Val Ala Met Gly Val Ala Pro Trp Gly
            180                 185                 190

Val Val Arg Asn Arg Asp Thr Leu Ile Asn Pro Lys Gly Ser Phe Pro
        195                 200                 205

Ala Arg Tyr Arg Trp Arg Gly Asp Pro Glu Asp Gly Val Gln Phe Pro
    210                 215                 220

Leu Asp Tyr Asn Tyr Ser Ala Phe Phe Leu Val Asp Asp Gly Thr His
225                 230                 235                 240

Gly Cys Leu Gly Gly Glu Asn Arg Phe Arg Leu Arg Leu Glu Ser Tyr
                245                 250                 255

Ile Ser Gln Gln Lys Thr Gly Val Gly Gly Thr Gly Ile Asp Ile Pro
            260                 265                 270

Val Leu Leu Leu Leu Ile Asp Gly Asp Glu Lys Met Leu Thr Arg Ile
        275                 280                 285

Glu Asn Ala Thr Gln Ala Gln Leu Pro Cys Leu Leu Val Ala Gly Ser
    290                 295                 300

Gly Gly Ala Ala Asp Cys Leu Ala Glu Thr Leu Glu Asp Thr Leu Ala
305                 310                 315                 320

Pro Gly Ser Gly Gly Ala Arg Gln Gly Glu Ala Arg Asp Arg Ile Arg
                325                 330                 335

Arg Phe Phe Pro Lys Gly Asp Leu Glu Val Leu Gln Ala Gln Val Glu
            340                 345                 350

Arg Ile Met Thr Arg Lys Glu Leu Leu Thr Val Tyr Ser Ser Glu Asp
        355                 360                 365

Gly Ser Glu Glu Phe Glu Thr Ile Val Leu Lys Ala Leu Val Lys Ala
    370                 375                 380

Cys Gly Ser Ser Glu Ala Ser Ala Tyr Leu Asp Glu Leu Arg Leu Ala
385                 390                 395                 400

Val Ala Trp Asn Arg Val Asp Ile Ala Gln Ser Glu Leu Phe Arg Gly
                405                 410                 415

Asp Ile Gln Trp Arg Ser Phe His Leu Glu Ala Ser Leu Met Asp Ala
            420                 425                 430

Leu Leu Asn Asp Arg Pro Glu Phe Val Arg Leu Leu Ile Ser His Gly
        435                 440                 445

Leu Ser Leu Gly His Phe Leu Thr Pro Met Arg Leu Ala Gln Leu Tyr
    450                 455                 460

Ser Ala Ala Pro Ser Asn Ser Leu Ile Arg Asn Leu Leu Asp Gln Ala
465                 470                 475                 480
```

```
Ser His Ser Ala Gly Thr Lys Ala Pro Ala Leu Lys Gly Ala Ala
            485                 490                 495

Glu Leu Arg Pro Pro Asp Val Gly His Val Leu Arg Met Leu Leu Gly
            500                 505                 510

Lys Met Cys Ala Pro Arg Tyr Pro Ser Gly Gly Ala Trp Asp Pro His
            515                 520                 525

Pro Gly Gln Gly Phe Gly Glu Ser Met Tyr Leu Leu Ser Asp Lys Ala
            530                 535                 540

Thr Ser Pro Leu Ser Leu Asp Ala Gly Leu Gly Gln Ala Pro Trp Ser
545                 550                 555                 560

Asp Leu Leu Leu Trp Ala Leu Leu Asn Arg Ala Gln Met Ala Met
                565                 570                 575

Tyr Phe Trp Glu Met Gly Ser Asn Ala Val Ser Ser Ala Leu Gly Ala
                580                 585                 590

Cys Leu Leu Leu Arg Val Met Ala Arg Leu Glu Pro Asp Ala Glu Glu
            595                 600                 605

Ala Ala Arg Arg Lys Asp Leu Ala Phe Lys Phe Glu Gly Met Gly Val
610                 615                 620

Asp Leu Phe Gly Glu Cys Tyr Arg Ser Glu Val Arg Ala Ala Arg
625                 630                 635                 640

Leu Leu Leu Arg Arg Cys Pro Leu Trp Gly Asp Ala Thr Cys Leu Gln
            645                 650                 655

Leu Ala Met Gln Ala Asp Ala Arg Ala Phe Phe Ala Gln Asp Gly Val
            660                 665                 670

Gln Ser Leu Leu Thr Gln Lys Trp Trp Gly Asp Met Ala Ser Thr Thr
            675                 680                 685

Pro Ile Trp Ala Leu Val Leu Ala Phe Phe Cys Pro Pro Leu Ile Tyr
            690                 695                 700

Thr Arg Leu Ile Thr Phe Arg Lys Ser Glu Glu Pro Thr Arg Glu
705                 710                 715                 720

Glu Leu Glu Phe Asp Met Asp Ser Val Ile Asn Gly Glu Gly Pro Val
                725                 730                 735

Gly Thr Ala Asp Pro Ala Glu Lys Thr Pro Leu Gly Val Pro Arg Gln
            740                 745                 750

Ser Gly Arg Pro Gly Cys Cys Gly Gly Arg Cys Gly Arg Arg Cys
            755                 760                 765

Leu Arg Arg Trp Phe His Phe Trp Gly Ala Pro Val Thr Ile Phe Met
            770                 775                 780

Gly Asn Val Val Ser Tyr Leu Leu Phe Leu Leu Leu Phe Ser Arg Val
785                 790                 795                 800

Leu Leu Val Asp Phe Gln Pro Ala Pro Pro Gly Ser Leu Glu Leu Leu
                805                 810                 815

Leu Tyr Phe Trp Ala Phe Thr Leu Leu Cys Glu Glu Leu Arg Gln Gly
            820                 825                 830

Leu Ser Gly Gly Gly Gly Ser Leu Ala Ser Gly Gly Pro Gly Pro Gly
            835                 840                 845

His Ala Ser Leu Ser Gln Arg Leu Arg Leu Tyr Leu Ala Asp Ser Trp
            850                 855                 860
```

-continued

```
Asn Gln Cys Asp Leu Val Ala Leu Thr Cys Phe Leu Gly Val Gly
865                 870                 875                 880

Cys Arg Leu Thr Pro Gly Leu Tyr His Leu Gly Arg Thr Val Leu Cys
                885                 890                 895

Ile Asp Phe Met Val Phe Thr Val Arg Leu Leu His Ile Phe Thr Val
            900                 905                 910

Asn Lys Gln Leu Gly Pro Lys Ile Val Ile Val Ser Lys Met Met Lys
        915                 920                 925

Asp Val Phe Phe Phe Leu Phe Phe Leu Gly Val Trp Leu Val Ala Tyr
930                 935                 940

Gly Val Ala Thr Glu Gly Leu Leu Arg Pro Arg Asp Ser Asp Phe Pro
945                 950                 955                 960

Ser Ile Leu Arg Arg Val Phe Tyr Arg Pro Tyr Leu Gln Ile Phe Gly
                965                 970                 975

Gln Ile Pro Gln Glu Asp Met Asp Val Ala Leu Met Glu His Ser Asn
            980                 985                 990

Cys Ser Ser Glu Pro Gly Phe Trp Ala His Pro Pro Gly Ala Gln Ala
        995                 1000                1005

Gly Thr Cys Val Ser Gln Tyr Ala Asn Trp Leu Val Leu Leu
    1010                1015                1020

Leu Val Ile Phe Leu Leu Val Ala Asn Ile Leu Leu Val Asn Leu
    1025                1030                1035

Leu Ile Ala Met Phe Ser Tyr Thr Phe Gly Lys Val Gln Gly Asn
    1040                1045                1050

Ser Asp Leu Tyr Trp Lys Ala Gln Arg Tyr Arg Leu Ile Arg Glu
    1055                1060                1065

Phe His Ser Arg Pro Ala Leu Ala Pro Pro Phe Ile Val Ile Ser
    1070                1075                1080

His Leu Arg Leu Leu Leu Arg Gln Leu Cys Arg Arg Pro Arg Ser
    1085                1090                1095

Pro Gln Pro Ser Ser Pro Ala Leu Glu His Phe Arg Val Tyr Leu
    1100                1105                1110

Ser Lys Glu Ala Glu Arg Lys Leu Leu Thr Trp Glu Ser Val His
    1115                1120                1125

Lys Glu Asn Phe Leu Leu Ala Arg Ala Arg Asp Lys Arg Glu Ser
    1130                1135                1140

Asp Ser Glu Arg Leu Lys Arg Thr Ser Gln Lys Val Asp Leu Ala
    1145                1150                1155

Leu Lys Gln Leu Gly His Ile Arg Glu Tyr Glu Gln Arg Leu Lys
    1160                1165                1170

Val Leu Glu Arg Glu Val Gln Gln Cys Ser Arg Val Leu Gly Trp
    1175                1180                1185

Val Ala Glu Ala Leu Ser Arg Ser Ala Leu Leu Pro Pro Gly Gly
    1190                1195                1200

Pro Pro Pro Pro Asp Leu Pro Gly Ser Lys Asp
    1205                1210
```